United States Patent
Århammar et al.

(10) Patent No.: US 12,419,816 B2
(45) Date of Patent: Sep. 23, 2025

(54) PARTICULATE AMORPHOUS MESOPOROUS MAGNESIUM CARBONATE MATERIAL

(71) Applicant: DISRUPTIVE MATERIALS OPERATIONS AB, Uppsala (SE)

(72) Inventors: Cecilia Århammar, Uppsala (SE); Gabriella Josefsson, Spånga (SE)

(73) Assignee: Disruptive Materials Operations AB, Uppsala (SE)

( * ) Notice: Subject to any disclaimer, the term of this patent is extended or adjusted under 35 U.S.C. 154(b) by 807 days.

(21) Appl. No.: 17/433,039

(22) PCT Filed: Feb. 25, 2020

(86) PCT No.: PCT/SE2020/050211
§ 371 (c)(1),
(2) Date: Aug. 23, 2021

(87) PCT Pub. No.: WO2020/176028
PCT Pub. Date: Sep. 3, 2020

(65) Prior Publication Data
US 2022/0160594 A1    May 26, 2022

(30) Foreign Application Priority Data
Feb. 25, 2019 (SE) .................... 1950239-2

(51) Int. Cl.
*A61K 8/19* (2006.01)
*A61K 8/02* (2006.01)
*A61Q 19/00* (2006.01)
*C01F 5/24* (2006.01)

(52) U.S. Cl.
CPC .............. *A61K 8/19* (2013.01); *A61K 8/0279* (2013.01); *A61Q 19/008* (2013.01); *C01F 5/24* (2013.01); *A61K 2800/412* (2013.01); *A61K 2800/651* (2013.01); *C01P 2002/72* (2013.01); *C01P 2004/03* (2013.01); *C01P 2004/51* (2013.01); *C01P 2004/61* (2013.01); *C01P 2006/12* (2013.01); *C01P 2006/14* (2013.01); *C01P 2006/19* (2013.01)

(58) Field of Classification Search
None
See application file for complete search history.

(56) References Cited

U.S. PATENT DOCUMENTS

| 8,084,506 B2 | 12/2011 | Zhao |
| 9,580,330 B2 | 2/2017 | Strömme et al. |
| 10,508,041 B2 | 12/2019 | Strömme et al. |
| 11,155,469 B2 | 10/2021 | Strömme et al. |
| 2005/0129606 A1 | 6/2005 | Matsuhashi et al. |
| 2015/0298984 A1 | 10/2015 | Strömme et al. |
| 2017/0151168 A1 * | 6/2017 | Constantine ............. A61K 8/29 |
| 2017/0152151 A1 | 6/2017 | Strömme et al. |
| 2017/0216181 A1 | 8/2017 | Aubert et al. |
| 2019/0008751 A1 | 1/2019 | Mustafa et al. |
| 2019/0106331 A1 | 4/2019 | Cheung et al. |
| 2019/0127232 A1 | 5/2019 | Cheung et al. |
| 2020/0048104 A1 | 2/2020 | Strömme et al. |

FOREIGN PATENT DOCUMENTS

| CN | 104837772 A | 8/2015 | |
| GB | 1218222 A | 1/1971 | |
| JP | 2519436 B2 * | 7/1996 | ............... A61K 8/19 |
| JP | 2005220058 A * | 8/2005 | |
| JP | 2018123129 A * | 8/2018 | |
| WO | 2017/174458 A1 | 10/2017 | |

OTHER PUBLICATIONS

Machine Translation of Susumu Google Patent [online]. 1996 [retrieved on May 8, 2024]. Retrieved from the Internet: <https://patents.google.com/patent/JP2519436B2/en?oq=JP+63159306+A> (Year: 1996).*
Machine Translation of HIbi Google Patent [online]. 2005 [retrieved on May 8, 2024]. Retrieved from the Internet: <https://patents.google.com/patent/JP2005220058A/en?oq=jp2005220058> (Year: 2005).*
Machine Translation of Shingo Google Patent [online]. [retrieved on May 8, 2024]. Retrieved from the Internet: <https://patents.google.com/patent/JP2018123129A/en?q=(powder+based+semi-solid%2c+liquid%2c+and+powder+spray+cosmetics+magnesium+carbonate)&oq=powder+based+semi-solid%2c+liquid> (Year: 2018).*
Rawlings, A.V. and Lombard, K.J. (2012), A review on the extensive skin benefits of mineral oil. Int J Cosmet Sci, 34: 511-518. https://doi.org/10.1111/j.1468-2494.2012.00752.x (Year: 2012).*
Radislav F, Dragica L, Mitar P, Ivan S, Oil absorption in mesoporous silica particles, (2010), Processing and Application of Ceramics 4 [4] (2010) 265-269 (Year: 2010).*
Alvebratt et al., "A Modified In Situ Method to Determine Release from a Complex Drug Carrier in Particle-Rich Suspensions", AAPS PharmSciTech, vol. 19, No. 7, pp. 2859-2865, Oct. 2018.
Yang et al., "Enhanced release of poorly water-soluble drugs from synergy between mesoporous magnesium carbonate and polymers", International Journal of Pharmaceutics 525 (2017) pp. 183-190.

(Continued)

*Primary Examiner* — Johann R Richter
*Assistant Examiner* — Afua Bamfoaa Boateng
(74) *Attorney, Agent, or Firm* — Morgan, Lewis & Bockius LLP

(57) ABSTRACT

The present invention relates to a particulate highly porous amorphous mesoporous magnesium carbonate material suitable for uptake of high amounts of oily substances, sebum or a beneficial agent or combinations of these and to topical and cosmetic compositions comprising such material. The particulate highly porous amorphous mesoporous magnesium carbonate material according to the invention has a total pore volume larger than 0.1 cm 3/g and is constituted of particles having a peak particle size at or below 35 μm.

21 Claims, 12 Drawing Sheets

(56) References Cited

OTHER PUBLICATIONS

Dening et al., "Novel Nanostructured Solid Materials for Modulating Oral Drug Delivery from Solid-State Lipid-Based Drug Delivery Systems", The AAPS Journal, vol. 18, No. 1, pp. 23-40, Jan. 2016.
Mintel, Database GNPD 2003, "Spray Anti-Perspirant Foot Talc", http://www.gnpd.com, XP055696052.
Mintel, Database GNPD 2009, "Finish Matte Pomade", http://www.gnpd.com, XP055696057.
Mintel, Database GNPD 2015, "Smooth Mat Base", http://www.gnpd.com, XP055696021.
Mintel, Database GNPD 2018, "Body Fresh Powder", http://www.gnpd.com, XP055696017.
Office Action dated Oct. 27, 2023, issued in corresponding Chinese Patent Application No. 202080015136.3.
International Search Report and Written Opinion dated Jun. 8, 2020, issued in corresponding International Patent Application No. PCT/SE2020/050211.
Office Action dated Mar. 31, 2023, issued in corresponding Chinese Patent Application No. 202080015136.3.

* cited by examiner

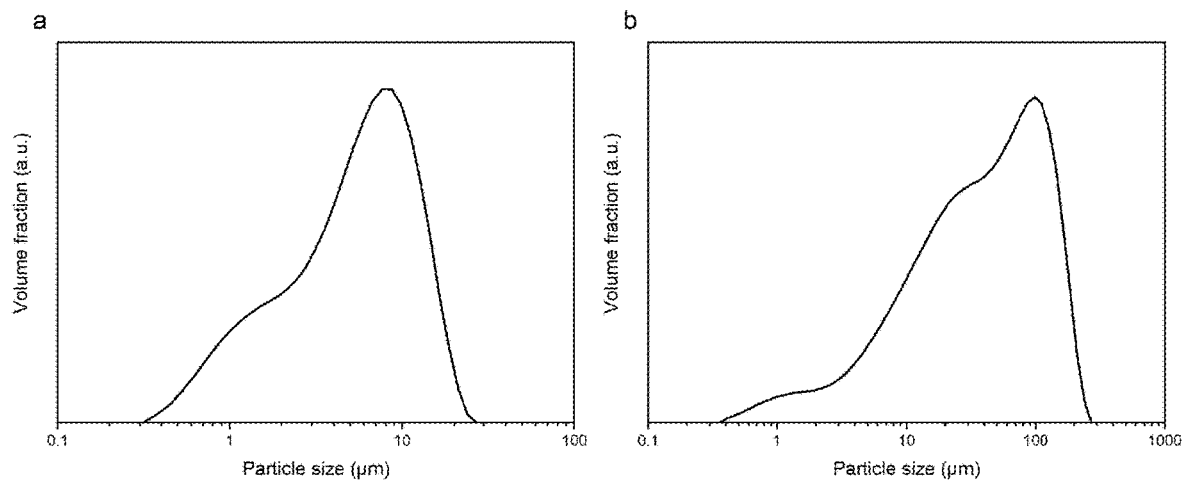
*Fig. 1 a-b*
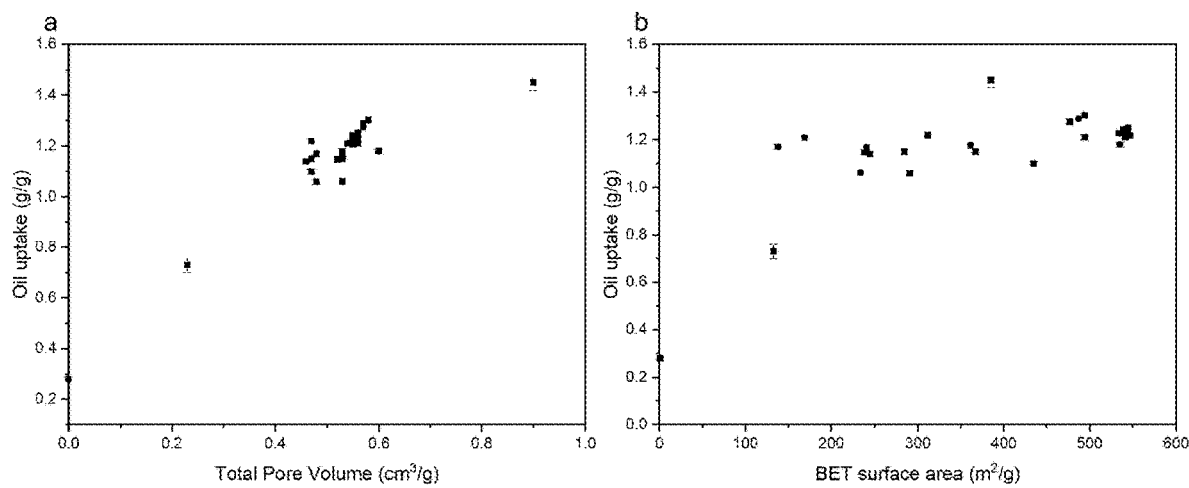
*Fig. 2a-b*

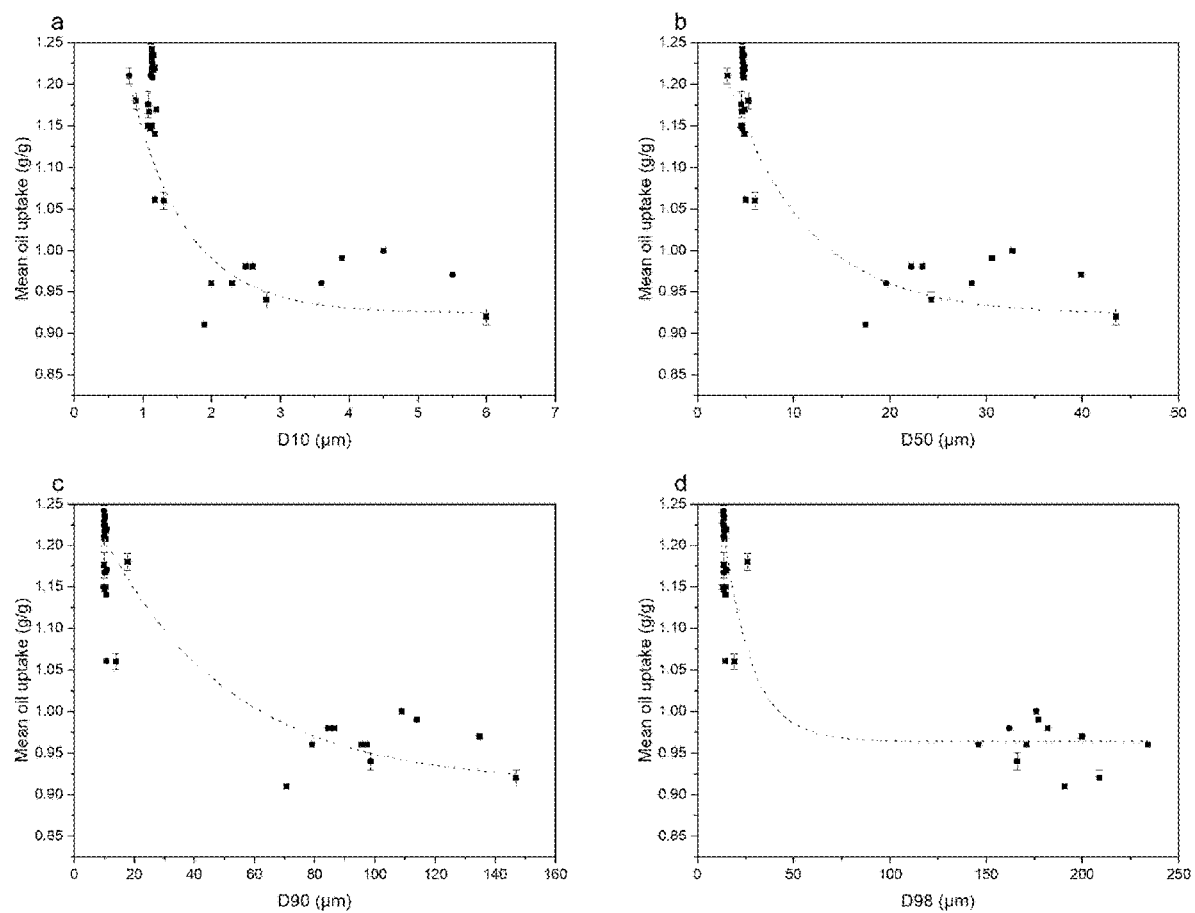
*Fig. 4a-d*

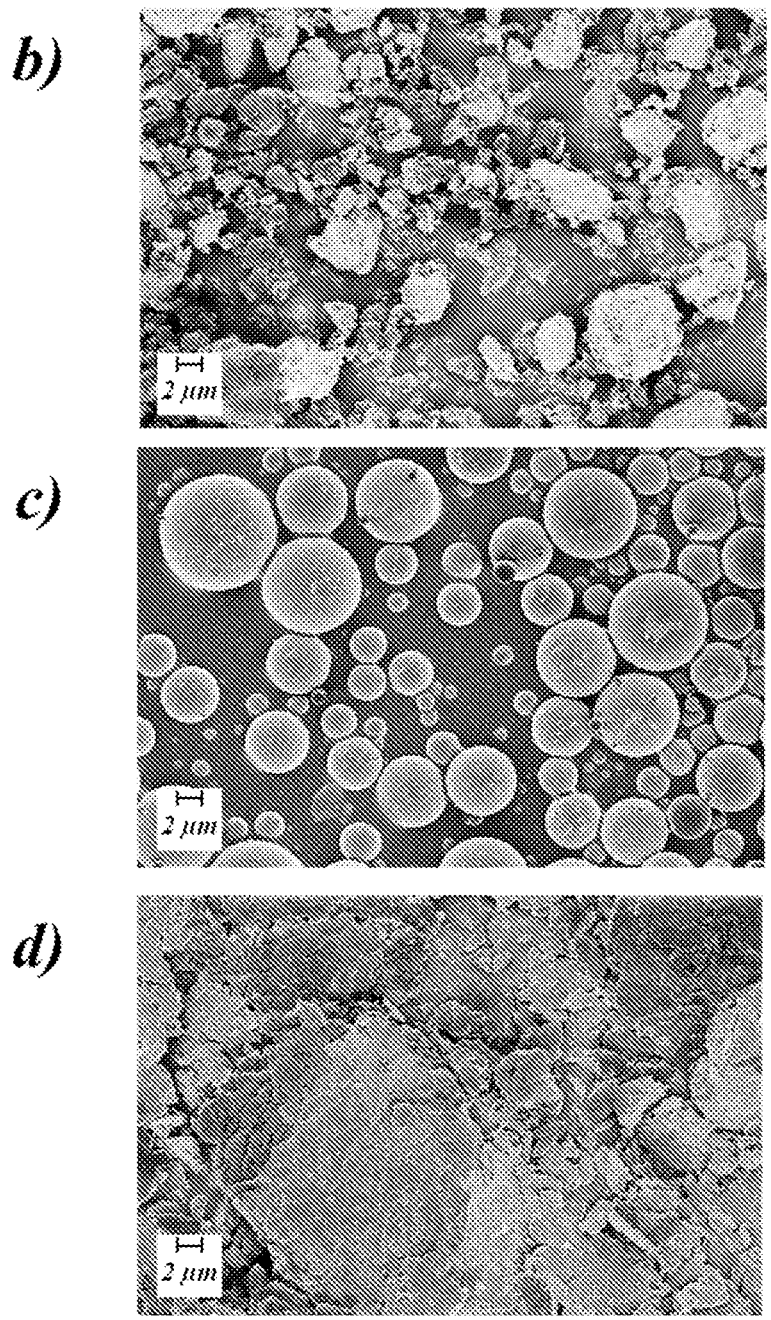
*Fig. 5b-d*

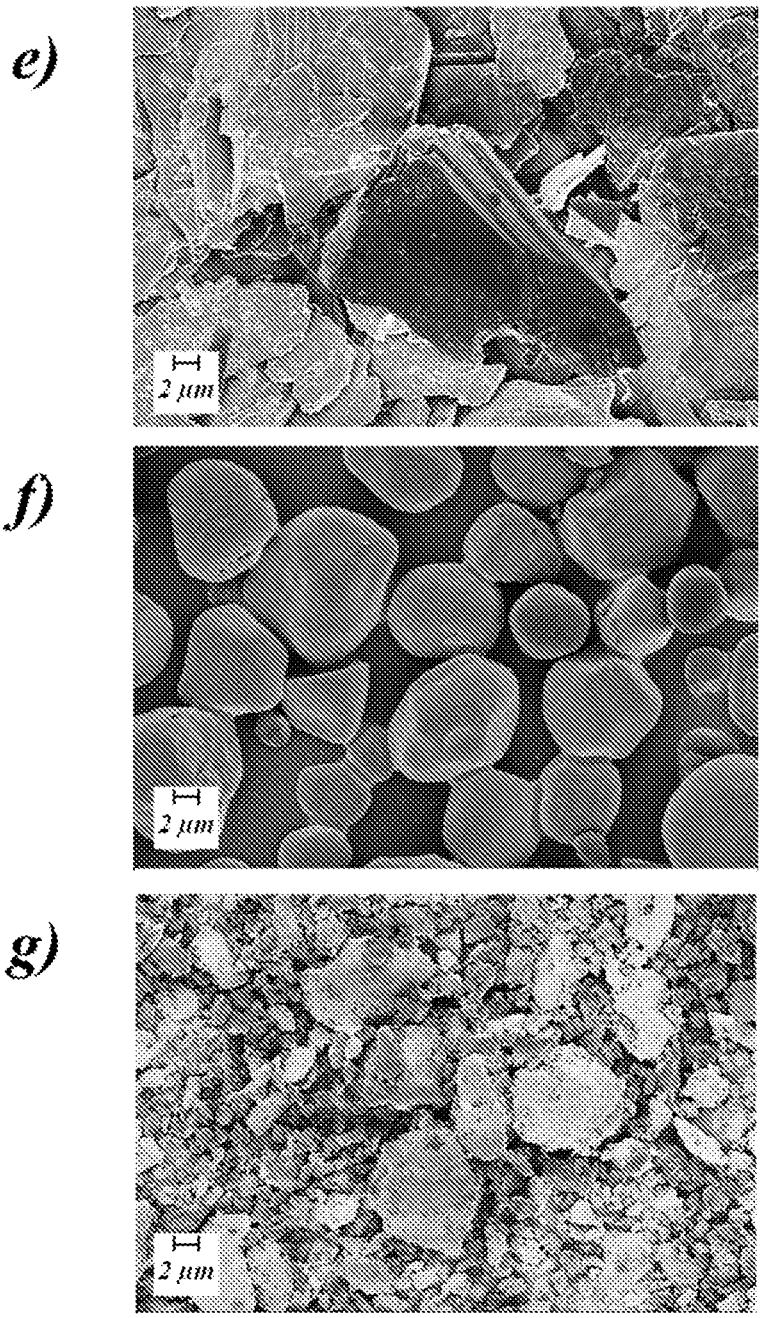
Fig. 5e-g

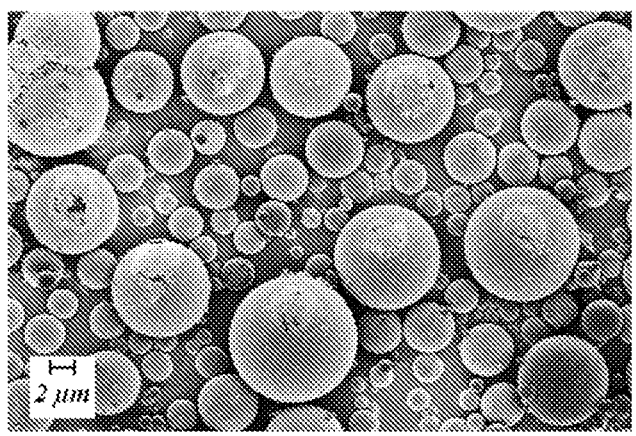
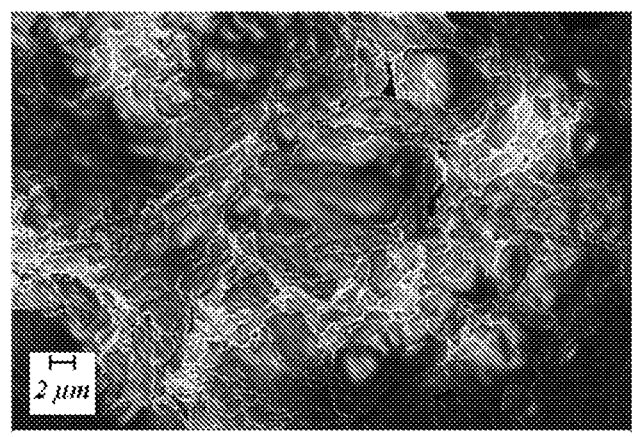
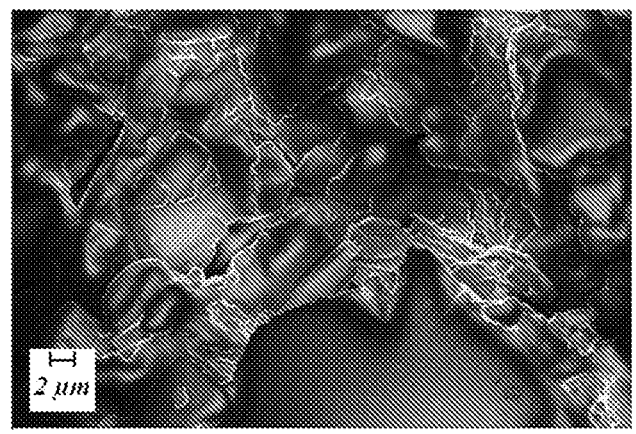
*Fig. 5h-j*

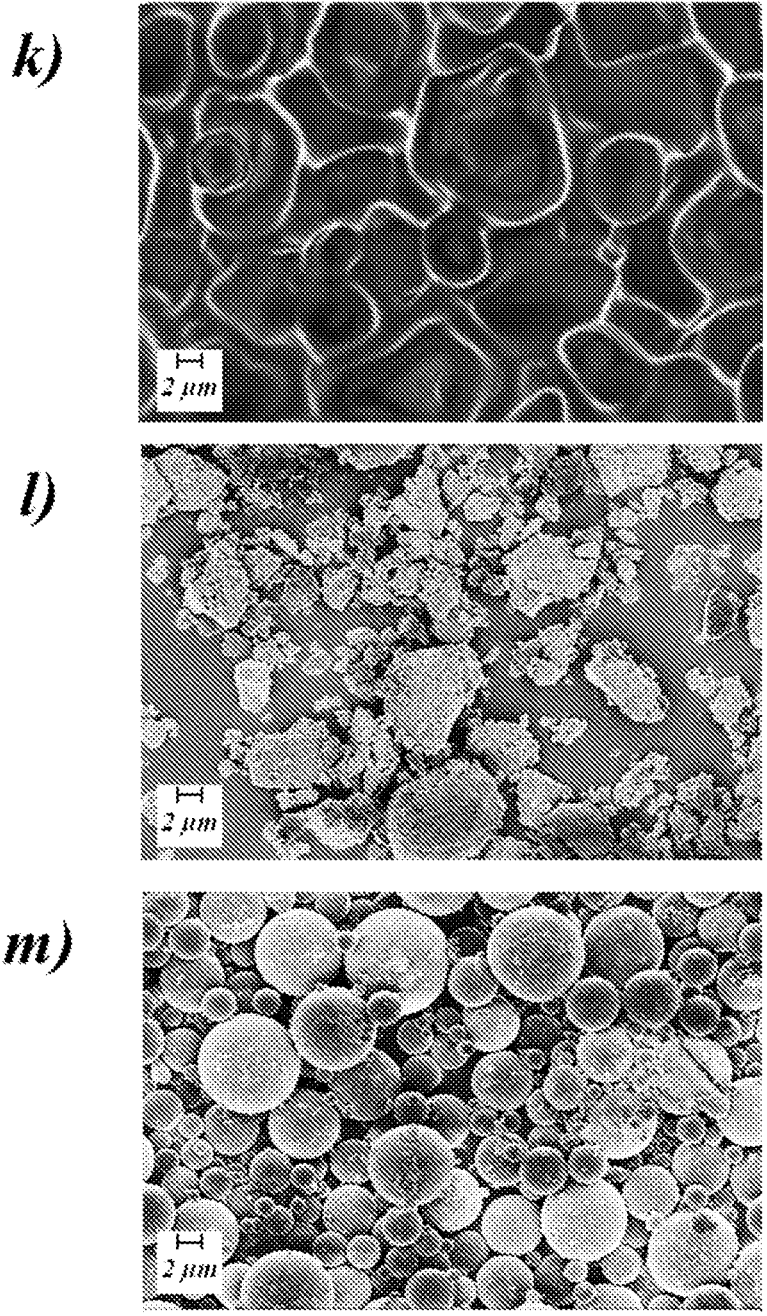
Fig. 5k-m

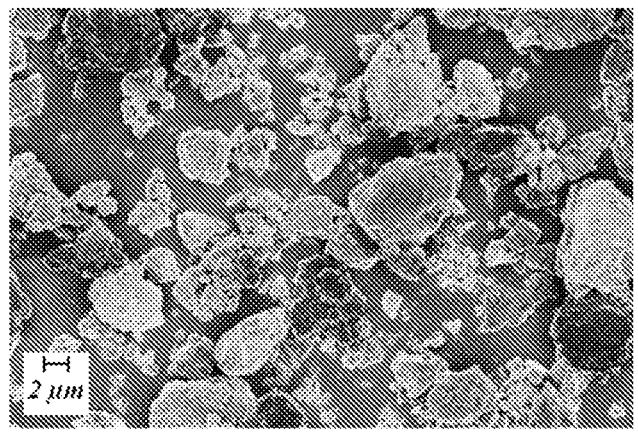
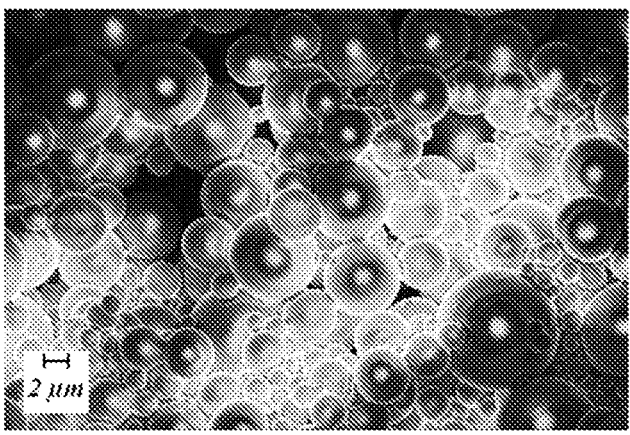
*Fig. 5n-o*

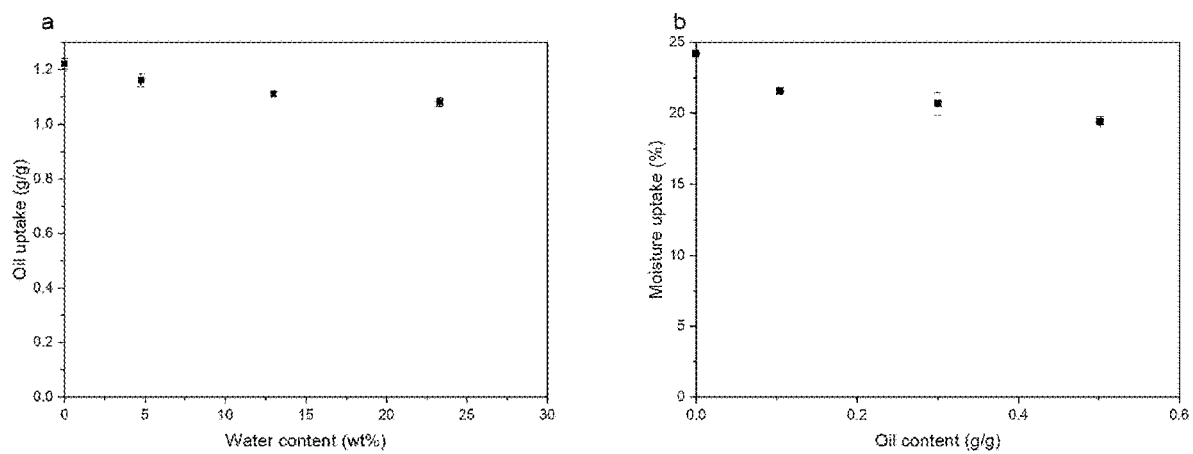
*Fig. 6a-b*

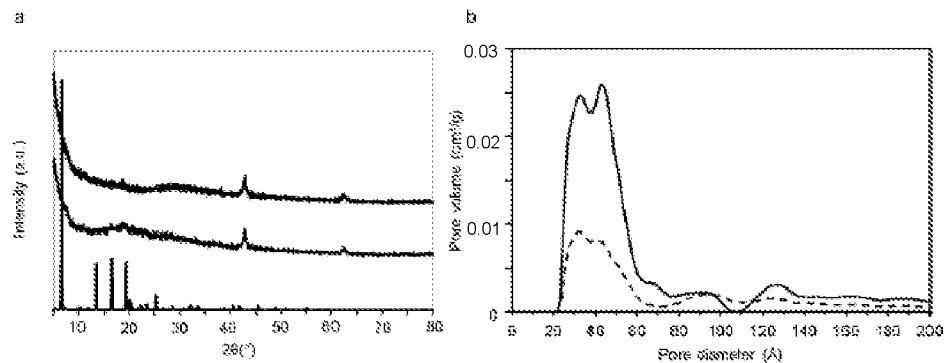
*Fig. 7 a-b*
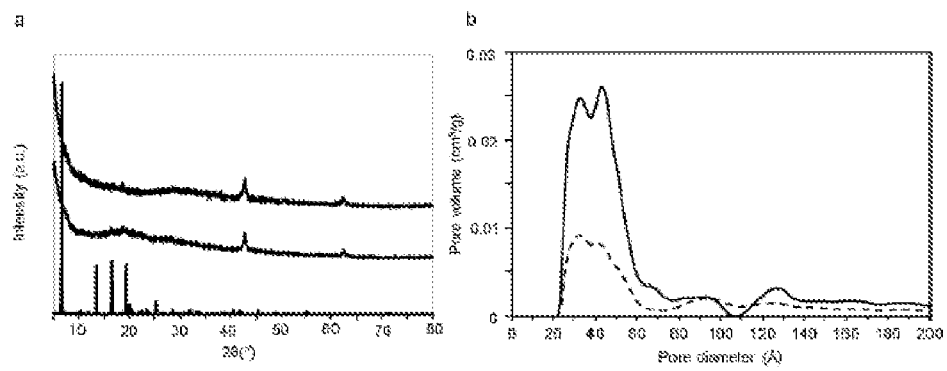
*Fig. 8 a-b*

PARTICULATE AMORPHOUS MESOPOROUS MAGNESIUM CARBONATE MATERIAL

FIELD OF THE INVENTION

The present invention relates to particles of highly porous amorphous Mesoporous Magnesium Carbonate (MMC) and compositions comprising such MMC and in particular a topical composition comprising such MMC. In particular the invention relates to particles of MMC optimized for uptake of oily substances such as sebum.

BACKGROUND OF THE INVENTION

Sebum is naturally occurring on human skin and is secreted from sebaceous glands located near the skin surface. Sebum is an oily or waxy matter with the function to lubricate and waterproof the skin and hair. In humans, the sebaceous glands occur in the greatest number on the face and scalp but exist in lesser numbers also on all parts of the skin. Sebum comprises primarily of triglycerides and fatty acids (57.5%), followed by wax esters (26%) and squalene (12%). The least abundant lipid in sebum is cholesterol, which with its esters, accounts for 4.5% of all total lipids.

An excess of sebum on the surface of the skin may cause the skin to look oily or shiny, which may appear unappealing. In addition, sebum build-up is associated with acne development and may highlight skin imperfections. Further, the sebum build-up reduces the fixation and long-lasting effect of cosmetic products such as powders, color cosmetics and foundations and may lead to smearing of the make-up. The sebum secreted from the sebaceous glands of the scalp makes the hair look oily or dirty.

To mitigate the sebum build-up, many cosmetic products, for example powders and foundations, comprise substances that are aimed to reduce the appearance of shiny or oily skin and to increase the long-lasting effect of cosmetic compositions. The predominant function utilized is that the added substance absorbs excess sebum. An important feature of a powder, for example, is that it should continuously absorb sebum and thereby retain the mattifying effect for many hours, preferably an entire day. Dry shampoos, for examples, function primarily by providing an absorbing substance in particulate form that take up excess sebum, making the hair look clean and non-greasy for a longer period.

A sebum absorbing component in a cosmetic composition must not only induce a long-lasting mattifying effect but should also improve the appearance of the skin and have a nice texture and feel upon application and during usage. Typically, large particles, particle size above a few hundred μm, may feel abrasive to the skin.

Common sebum-absorbing cosmetic products comprises mineral substances and/or organic substances as sebum absorbers. Examples of sebum absorbers are starches, calcium silicates, perlites, zeolites, poly lactic acids, silicas, polyamide powders, powders of acrylic polymers, silicone elastomer powders, mica powders, kaolin clays, talc or combinations thereof.

U.S. Pat. No. 8,084,506 discloses a cosmetic composition comprising at least 5% by weight of the composition of a silica containing compound as a sebum absorbing component.

US 2017/0216181 discloses a hair cleaning aerosol product comprising particulate porous silica micro spheres as sebum absorber. The silica particles have a BET surface area from approximately 150 $m^2/g$ to 600 $m^2/g$, and the size of the silicate particles is preferably less than 20 μm. The product may also include "styling powder" apart from the sebum absorber, the styling powder added for hair styling purposes. Styling powders include for example silicates, calcium carbonate, magnesium carbonate, alumina, barium sulfate and/or magnesium oxide with particle sizes from 20 to 50 μm.

Amorphous mesoporous magnesium carbonate (MMC) has attracted attention as a highly effective absorbing material and as a carrier of substances loaded into the material. MMC is a highly porous material composed of amorphous magnesium carbonate and magnesium oxide. The specific surface area of MMC can be from 100 $m^2/g$ up to 800 $m^2/g$ (BET), the total pore volume larger than 0.1 $cm^3/g$ and the average pore size can be varied from 2 to 30 nm, by tuning the synthesis conditions. The material has also been shown to be non-cytotoxic, showing no toxicity to human dermal fibroblast cells at concentrations of 1000 μg/ml and below, and induces no skin irritation when tested in vivo.

U.S. Pat. No. 9,580,330 relates to an X-ray amorphous mesoporous magnesium carbonate (MMC) with large specific surface area and extraordinary moisture sorption capacity. The material is suggested for various uses, including but not limited to delivery and carrier systems for therapeutic and cosmetic or volatile agents. U.S. Pat. No. 9,580,330 further discuss that MMC can be used in a cosmetic composition for the adsorption of fat, oil and impurities from the skin.

WO2017/174458 discloses a method of controlling several characteristic parameters of an X-ray amorphous mesoporous magnesium carbonate including the pore size. The mesopores are in the range from 10 nm to 30 nm. A surface area larger than 120 $m^2/g$ and a total pore volume larger than 0.5 $cm^3/g$ is reported.

In order for MMC to be suitable for cosmetic products, for example, the material must meet high requirements of appearance and sensory characteristics in combination with the ability to take up sebum and sweat, for example.

SUMMARY OF THE INVENTION

The object of the invention is to provide a material or material composition with improved oily substance uptake, such as uptake of sebum from skin or scalp, for topical use including cosmetics, hair care, skin-care, sun-protection, medical or other topical application. Further, it would be advantageous if the other properties of the MMC such as adsorption of moisture or water as well as the ability of MMC of being a carrier of loaded substances could be combined with an increased uptake of oily substances.

This is achieved by the particulate highly porous amorphous mesoporous magnesium carbonate material as defined in claim 1 and the method of production as defined in claim 19.

The particulate highly porous amorphous mesoporous magnesium carbonate material according to the invention exhibits an improved uptake of oily substances. The material has a total pore volume larger than 0.1 $cm^3/g$, a specific surface area between 100 and 800 $m^2/g$ (BET) and is constituted of particles having a peak particle size at or below 35 μm.

According to aspects of the invention the particulate highly porous amorphous mesoporous magnesium carbonate material has a peak particle size between 1 and 35 μm, preferably between 1 and 30 μm, and even more preferably between 1 and 20 μm.

According to aspects of the invention the particulate highly porous amorphous mesoporous magnesium carbonate material the total pore volume of the particulate highly porous amorphous mesoporous magnesium carbonate material is larger than 0.1 cm$^3$/g, preferably larger than 0.2 cm$^3$/g, and even more preferably larger than 0.3 cm$^3$/g.

According to one aspect of the invention the particulate highly porous amorphous mesoporous magnesium carbonate material has a $D_{50}$ value below 20 μm.

According to one aspect of the invention the particulate highly porous amorphous mesoporous magnesium carbonate material is capable of a combined uptake of an oily substance and a hydrophilic substance. The uptake of an oily substance above 0.5 g oil per g material with a combined moisture uptake of at least 5 wt %.

According to one aspect of the invention the particulate highly porous amorphous mesoporous magnesium carbonate material is loaded with an agent. The agent may be an oily substance, a beneficial agent an active substance or combinations of these. The active substance may be an active pharmaceutical agent (API).

According to one aspect of the invention a topical composition is provided comprising the particulate highly porous amorphous mesoporous magnesium carbonate material.

According to one aspect of the invention a cosmetic composition is provided comprising the particulate highly porous amorphous mesoporous magnesium carbonate material.

According to aspects of the invention topical or cosmetic products are provided comprising the particulate highly porous amorphous mesoporous magnesium carbonate material. Such products include, but are not limited to loose powders, pressed powders, foundations and dry shampoos.

According to aspects of the invention topical or cosmetic dry powder products are provided comprising the particulate highly porous amorphous mesoporous magnesium carbonate material and an oily substance and or oily substances at a concentration up to 1 g/g MMC powder.

According to aspects of the invention a loose powder product is provided comprising particulate MMC and an oily substance up to 0.75 g oil/g MMC powder, or at least up to 0.5 g oil/g MMC powder. Thanks to the superior oil uptake capabilities of the particulate MMC according to the invention the loose powder characteristics are preserved at these high oily substance uptakes.

According to aspects of the invention a powder spray product is provided comprising particulate MMC according to the invention and an oily substance up to 0.75 g oil/g MMC powder, or at least up to 0.5 g oil/g MMC powder. Thanks to the superior oil uptake capabilities of the particulate MMC according to the invention a spray product can be provided at these high oily substance uptakes.

According to one embodiment of the invention a pressed powder product is provided comprising particulate MMC according to the invention and an oily substance up to 1.0 g oil/g MMC powder, or at least up to 0.75 g oil/g MMC powder. Thanks to the superior oil uptake capabilities of the particulate MMC according to the invention the pressed powder characteristics are preserved at these high oily substance uptakes.

According to one embodiment of the invention a semi-solid product is provided comprising particulate MMC according to the invention and an oily substance up to 1.25 g oil/g MMC powder, or at least up to 1.0 g oil/g MMC powder. Thanks to the superior oil uptake capabilities of the particulate MMC according to the invention the characteristics of a typical semi-solid are preserved at these high oily substance uptakes.

According to one embodiment of the invention a liquid product is provided comprising particulate MMC according to the invention and an oily substance up to 1.25 g oil/g MMC powder, or at least up to 1.0 g oil/g MMC powder.

Thanks to the invention, a particulate MMC material according to the invention is provided that exhibit an increased capacity for uptake of oil, oily substances and/or sebum.

One advantage is that a powder comprising the particulate MMC material, according to the invention, maintains a matte appearance even after adsorbing high amounts of sebum.

A further advantage is that a topical composition comprising the particulate MMC material can be used as carrier of beneficial or active substances used in e.g. skin-care, hair-care, sun-protection, or for treating a skin-condition or dermal disease or damage.

A further advantage is that the particulate MMC material can easily be loaded with high amounts of beneficial oils, oily substances or chemicals dissolved in an oil, by utilizing the porous structure and oil-absorbing properties of the particulate MMC material.

A further advantage is that a powder or similar product comprising the particulate MMC material can take up sebum and have a matte appearance on the skin even if the MMC is loaded with beneficial or active substances.

A further advantage is that the loaded particulate MMC, even if loaded with an oily substance, typically maintains much of its capability for taking up an oily substance such as sebum.

A further advantage is that the particulate MMC material combines an uptake of oil/oily substance with an uptake of moisture, which makes it possible to simultaneously control the oil and moisture levels or to load the material with a hydrophilic agent and still maintain the oil uptaking properties and vice versa. This makes it possible to provide topical and/or cosmetical products with an ability to deliver hydrophilic or hydrophobic substances to the skin or scalp, for example, and at the same time take up for example sebum and/or sweat.

A further advantage is that the particulate MMC material can be added to an oily liquid formulation, as a mattifying agent, to reduce its oily appearance and give beneficial sensory characteristics.

A further advantage is that the particulate MMC material can be combined with an oily liquid formulation to provide a dry powder product. Thereby it is possible to provide dry powder products with substances that previously only could be provided in liquid or semisolid formulations such as solutions, creams/emulsions, lotions or ointments/pastes.

When loading MMC with a substance of limited solubility, the maximum concentration of that substance may be increased in a liquid formulation. As an example, absorbing an oily substance into MMC may enable higher amounts of this substance than if it was included directly into an o/w formulation with low amount of oil phase.

In the following, the invention will be described in more detail, by way of example only, with regard to non-limiting embodiments thereof, reference being made to the accompanying drawings and graphs.

BRIEF DESCRIPTION OF THE DRAWINGS

FIG. 1a-b: Peak particle size distributions showing peak size of a) 8 and b) 98 μm;

FIG. 2a-b: Oil uptake as a function of total a) pore volume and b) BET surface area for particles with a peak particle size between 6 and 10 μm;

FIG. 4: Oil uptake as a function of particle size distributions a) $D_{10}$, b) $D_{50}$, c) $D_{90}$ and d) $D_{98}$ for milled materials (ball-milling and jet-milling);

FIG. 5a-o: Photographs (a) and SEM images (b-o) of particulate MMC according to the invention, corn starch, talc, kaolin and mesoporous silica, pure (non-mixed) materials and materials mixed with increasing amounts of oil, a) photograph/graph of corn starch, talc, kaolin, mesoporous silica and particulate MMC at increasing amounts of oil, b) pure particulate MMC, c) pure mesoporous silica, d) pure kaolin, e) pure talc, f) pure corn starch, g) particulate MMC mixed with 0.25 g oil/g material, h) mesoporous silica mixed with 0.25 g oil/g material, i) kaolin mixed with 0.25 g oil/g material, j) talc mixed with 0.25 g oil/g material, k) corn starch mixed with 0.25 g oil/g material, l) particulate MMC mixed with 0.50 g oil/g material, m) mesoporous silica mixed with 0.50 g oil/g material, n) particulate MMC mixed with 0.75 g oil/g material, and o) mesoporous silica mixed with 0.75 g oil/g material;

FIG. 6a-b: a) Uptake of oil after addition of water to the particulate MMC according to the invention and b) moisture uptake after oil uptake;

FIG. 7a-b: Particulate MMC according to the invention loaded with 30 wt % trans-resveratrol, a) XRD-patterns and b) pore volume as a function of pore size;

FIG. 8a-b: Particulate MMC according to the invention loaded with trans-retinol, a) XRD patterns and b) pore volume as a function of pore size.

DETAILED DESCRIPTION

Figure 3:
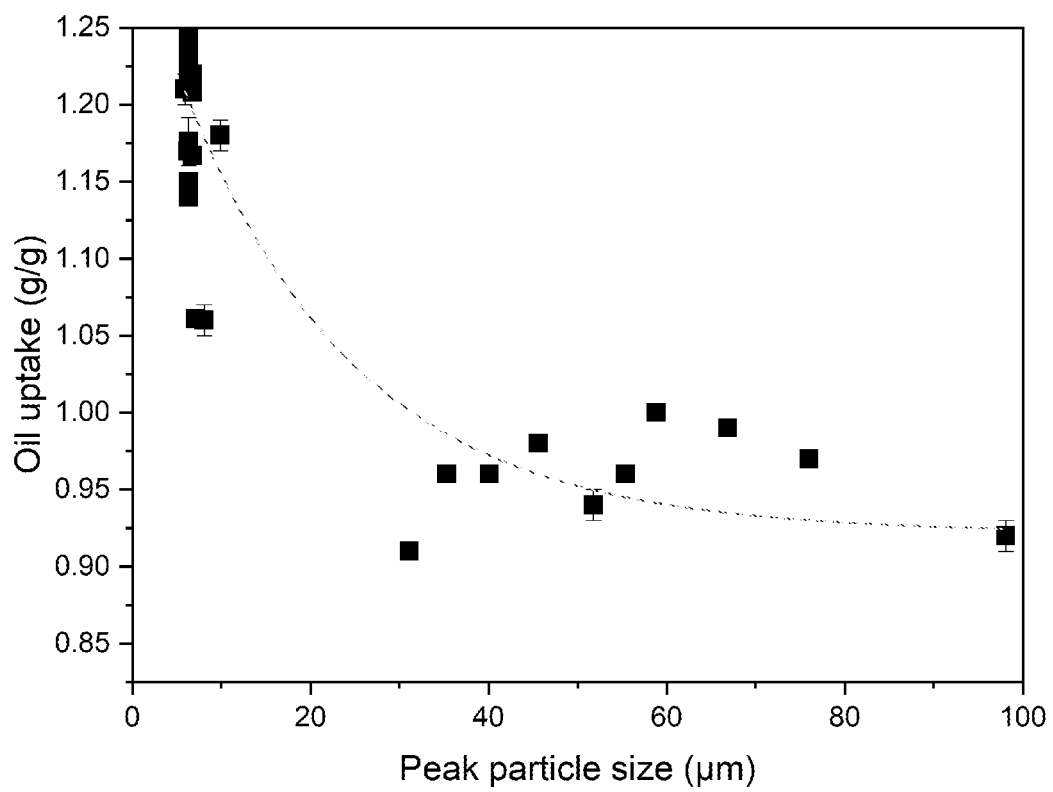
FIG. 3: Oil uptake as a function of peak particle size for milled materials (ball-milling and jet-milling)

The term "topical composition" used herein means a composition which is intended to be applied onto the consumer's skin, for example onto the facial skin, or provided on consumer's hair and/or scalp. Discussed herein is primarily the function related to uptake of an oily substance. As appreciated by the skilled person a topical composition may comprise a number of components providing a large number of different functions, for example, but not limited to, other particulate materials, minerals, fillers, binders, fragrances, active ingredients, liquids, silicones, emollients. The topical composition is applied topically on skin or scalp for the use in cosmetics, skin care, hair care, or medical care to improve appearance of skin, treat different skin-conditions or disease and/or to protect against UV-rays from the sun. The term topical composition includes cosmetic compositions.

The term "topical product" used herein refers to consumer products for topical use comprising a topical composition. Topical products include, but is not limited to color cosmetic products, hair care products, skin care products and personal care products. One type of topical product is a dry powder product provided as a powder formulation for example a pressed or loose powder or a powder spray. Another type of product format may be referred to as liquid formulations, including for example solutions, creams/emulsions, lotions or ointments/pastes. A third type of formulation is a semi-solid formulation, including for example silicones and waxes. A topical product may further include compositions to treat skin conditions or disease. Topical products may be applied to the skin, hair or mucous membrane by hand or by other means of administration, for example by spraying, brush or sponge for e.g. loose or pressed powders, sticks, liquid formulations and powder sprays.

In the following topical and cosmetic products of different categories in which the particulate MMC according to the invention will be discussed. The product categorizes include, but is not limited to:

A loose powder product is a dry powder product characterized by fine free-flowing particles that usually is provided in ajar.

A pressed powder product is a dry powder product that is compressed into compact form. It may contain ingredients such as silicones and waxes that facilitate the formation of the pressed compact powder form. Face powder in the form of a pressed power cake is an example of a common pressed powder product.

A powder spray are powders that come in a spray bottle. In a powder aerosol spray, the powder is dispersed in a suspension of fine solid particles or liquid droplets, in air or another gas.

A liquid product is provided in the form of a semi-viscous or viscous medium, for example hydrous or anhydrous solutions, oil-in-water or water-in-oil emulsions (cream or lotion), suspensions, ointments, gels or pastes.

A semi-solid product is at room temperature neither solid or liquid, for example a wax or a thick paste. Silicones and waxes are typically used to turn the powder product into a semi-solid. A stick an a cake are an examples of semi-solid products.

MMC refers herein to a highly porous amorphous mesoporous magnesium carbonate with a total pore volume larger than 0.1 $cm^3$/g and typically below 1.2 $cm^3$/g. The material typically has a specific surface area between 100 and 800 $m^2$/g (BET), and an average pore size between 2 and 30 nm. The MMC may comprise up to 30 wt % of magnesium oxide (MgO) and unavoidable impurities and additives as a result of for example impurities in the raw material, the production process and/or storage conditions. Impurities include but is not limited to $Mg(OH)_2$. MMC as produced according to prior art is a powder with irregularly shaped particles. The particle sizes can be controlled by various sieving or milling techniques.

The particulate highly porous amorphous mesoporous magnesium carbonate material, or particulate MMC material, according to the invention refers herein to a further processed material for providing a fractionized particulate material by sieving or milling, for example. The particulate MMC material has a total pore volume larger than 0.1 $cm^3$/g and typically below 1.2 $cm^3$/g. The material typically has a specific surface area between 100 and 800 $m^2$/g (BET), and an average pore size between 2 and 30 nm. The MMC may comprise up to 30 wt % of magnesium oxide (MgO) and, unavoidable impurities and additives.

The term "agent" used herein refers to a substance or any compound present in a cosmetic, or topical composition, which produces a beneficial effect perceived by the consumer during the use thereof and/or obtained on the consumer product itself, said beneficial effect possibly being a sensorial improvement or an especially visual and/or olfactory and/or tactile modification, an improvement in comfort and/or ease of application, an aesthetic effect, a hygienic effect, a clean feel, a curative/medical effect, a UV-absorbing effect and/or a protective or prophylactic effect.

The term "active substance" used herein refers to an agent that is a biologically active substance or compound then administrated to a mammal, or active pharmaceutical ingredient (API). The administration including but not limited to topical administration for example administration to a body surface such as the skin and internal administration, for example oral administration.

The term "active pharmaceutical agent (API)" used herein refers to an active substance with acknowledged pharmaceutical effect.

The term "beneficial agent" used herein refers to an agent that may be characterized as giving non-medical effects in a topical composition. The beneficial agent is a substance or any compound present in a consumer cosmetic product, which produces a beneficial effect perceived by the consumer during the use thereof and/or obtained on the consumer product itself, said beneficial effect possibly being a sensorial improvement or an especially visual and/or olfactory and/or tactile modification, an improvement in comfort and/or ease of application, an aesthetic effect, a hygienic effect, a clean feel, a curative and/or a protective or prophylactic effect.

The term "oil" means any non-polar chemical substance that is an oily viscous liquid at ambient temperature and is both hydrophobic and lipophilic. It includes classes of chemical compounds that may be otherwise unrelated in structure, properties, and uses. Oils may for example be of animal, vegetable, or synthetic origin.

The term "oily substance" used herein refers to a substance comprising oil, fatty acids, lipids, esters etc as well as other substances, for example chemicals dissolved in an oil. Oily substances include, but are not limited to sebum, a vegetable oil, a mineral oil, an animal oil, a silicone oil, an essential oil, a fat or a wax.

The oily substance may also, or alternatively, be a carrier of an agent, the agent dissolved or dispersed in the oily substance. The agent may, but is not limited to, an antioxidant such as a trans-retinol, trans-resveratrol or an oil-soluble vitamin. The agent may also, but is not limited to, an aroma compound such as an ester, an aromatic or a terpene.

The abbreviation "wt %" means % by weight, which is the weight fraction of a component in relation to the total weight of a mixture including the component, expressed in percent.

It is herein recognized that a provided particulate MMC material always will be constituted of particles with variation in size and shape. The particle size of the MMC can be characterized by a particle size distribution, wherein the particle size distribution will depend at least on the method of production and treatments to control the size distribution such as sieving and/or milling. Particle size distribution may be measured using laser diffraction technique and commercially instruments are readily available, for example from Malvern Panalytical. The term "peak particle size" used herein refers to the position, in particle size, of the peak representing the largest volume fraction in a particle size distribution of a particulate MMC material. Size refers to the mean equivalent spherical diameter of particles as measured by laser diffraction, for example using the Malvern Panalytical instrument. Particle size distribution is further often characterized with so called D-values, also used herein, wherein $D_{10}$ (X) means 10 volume % are particles with a size smaller than the number X, $D_{50}$ (Y) means 50 volume % are particles with a size smaller than the number Y, $D_{90}$ (Z) means 90 volume % are particles with a size smaller than the number Z, etc.

The particulate MMC material's uptake of an oily substance was investigated and the result presented in Table 1-2 and illustrated in the graphs of FIGS. 2-4. Experimental details are given below. The uptake of an oily substance was shown to be essentially independent on the particle size for peak particle sizes above 35 μm, but significantly increased for small peak particle sizes with an onset of the uptake of an oily substance at 35 μm. Both the independence of particle size for particles above 35 μm and the very rapid increase to a considerably higher level of oil uptake for particle size below 35 μm, differs dramatically from what could be expected by only considering an increase of total surface area of the particular material as the particle size is reduced. Such particle size/surface area driven effect caused by a decrease in particle size can only be expected to give a continuous and uniform dependence on oil uptake with decreasing particle size. In the present invention MMC consists of small particles with large pore volume which, without being bound by theory, is believed to lead to the abrupt increase in oil uptake compared to other non-porous materials.

The particulate MMC material according to the invention for improved uptake of oily substance has a peak particle size at or below 35 μm. Preferably the peak particle size is between 1 and 35 μm, more preferably between 1 and 30 μm and even more preferably between 1 and 20 μm. The particulate MMC material has an average pore size between 2 and 30 nm, a specific surface area between 100 and 800 m$^2$/g (BET) and a total pore volume of above 0.1 cm$^3$/g, preferably above 0.2 cm$^3$/g, and even more preferably above 0.3 cm$^3$/g, and typically below 1.2 cm$^3$/g. The onset of the increase in oily substance uptake at the peak particle size of 35 μm corresponds to a $D_{10}$-value of 3 μm, a $D_{50}$-value of 20 μm and a $D_{90}$-value of 96 μm.

Having small particle sizes in for example a topical product is advantageous also from how the product is perceived by the customer. Large particles make the product feel coarse and unpleasant, whereas a smooth feel is associated with small particles.

According to one embodiment of the invention the particulate MMC material is a component in a topical composition with the purpose of taking up and holding sebum, oil or an oily substance. Examples of topical products comprising a topical composition of the invention include, but are not limited to, cosmetic powder and dry shampoo.

According to one embodiment of the invention the particulate MMC material is a component in a composition which has been loaded with an oily substance, wherein the oily substance is an agent, or an agent that has been dissolved or dispersed in the oily substance, for example a lipophilic substance. Examples of topical products according to this embodiment of the invention include, but are not limited to, anti-aging skin care products, and products to treat different skin conditions such as acne.

According to one embodiment of the invention the particulate MMC material is loaded with an agent. As compared with the above embodiment, the agent does, in this embodiment, not need to be in the form of an oily substance. According to the embodiment the loaded particulate MMC material can be loaded with up to 1 g agent/g MMC material (i.e. 50 wt % loading) and is still capable of taking up an oily substance, sebum for example, even in the loaded state.

According to one embodiment of the invention the particulate MMC material is a component in a topical composition and the agent is a beneficial agent.

According to one embodiment of the invention the particulate MMC material is a component in a topical composition and the agent is an active substance.

According to one embodiment the particulate MMC material is an additive to an oily composition, wherein the particulate MMC functions as a mattifying agent. Thereby the oily composition may have the oily character but a non-oily appearance.

It is desirable to provide cosmetic and topical products as dry powder products, for example as loose powders, pressed powders and dry shampoo. The particulate MMC material uptake of an oily substance in relation to the powder characteristics of the material was investigated and compared with other known absorbing materials used in cosmetic and topical products and the results are presented in Table 3 and illustrated in the photographs and SEM images in FIG. 5 a-o. The ability of the particulate MMC according to the invention, to take up higher levels of oily substances with maintained powder characteristics, as compared to common prior art absorbent cosmetic materials may be advantageously utilized to provide new or improved topological and cosmetic powder products. The possibility to provide oily substances in a dry powder form significantly widens the usability of these substances as their positive effects on the skin, for example, may be utilized without the skin having an oily appearance often associated with these substances. The amount of an oily substance, which can be included into a formulation, may also not be as limited by the amount of oil phase in the formulation but can be included up to the maximum inclusion level into MMC.

According to aspects of the invention topical or cosmetic dry powder products are provided comprising the particulate highly porous amorphous mesoporous magnesium carbonate material and an oily substance or oily substances at a concentration up to 1 g oil/g material.

According to one embodiment of the invention a loose powder product is provided comprising particulate MMC according to the invention and an oily substance up to 0.75 g oil/g MMC powder, or at least up to 0.5 g oil/g MMC powder.

According to one embodiment of the invention a powder spray product is provided comprising particulate MMC according to the invention and an oily substance up to 0.75 g oil/g MMC powder, or at least up to 0.5 g oil/g MMC powder.

According to one embodiment of the invention a pressed powder product is provided comprising particulate MMC according to the invention and an oily substance up to 1.0 g oil/g MMC powder, or at least up to 0.75 g oil/g MMC powder.

According to one embodiment of the invention a semi-solid product is provided comprising particulate MMC according to the invention and an oily substance up to 1.25 g oil/g MMC powder, or at least up to 1.0 g oil/g MMC powder.

According to one embodiment of the invention a liquid product is provided comprising particulate MMC according to the invention and an oily substance up to 1.25 g oil/g MMC powder, or at least up to 1.0 g oil/g MMC powder.

The ability of the particular MMC according to the invention to provide a dry powder product can further be utilized also for agents and active substances not typically provided in the form of an oily substance, if such an agent/active substance is first dissolved in an oily substance, to give a blend of oily substance and agent that is received by the particulate MMC. A non-limiting example would be trans-retinol dissolved in oil.

According to one embodiment of the invention the particulate highly porous amorphous mesoporous magnesium carbonate material is capable of a combined uptake of oily substance and a hydrophilic substance, for example water or moisture, which is illustrated in FIG. 6a-b. The uptake of an oily substance is above 0.5 g oil per g MMC material containing at least 5 wt % moisture.

The method according to the invention of preparing a particulate MMC material comprises initial steps known in the art, for example from WO2017/174458 of preparing an MMC. These initial steps comprise:
  (i) mixing magnesium oxide (MgO) and methanol under a pressure of 0.5-5 bar, and at a temperature of 10-70° C. for 12-36 hours, providing a gel;
  (ii) drying the gel of step (ii) at 50-105° C., providing particles;
  (iii) finally drying the particles obtained in step (ii) at a temperature up to 300° C.; and According to the method of the present invention a further step according to the present invention is introduced:
  (iv) fractionizing the particles obtained in step (iii) to a predetermined peak particle size, the predetermined peak particle size being at or below 35 μm,
    for example, by milling the particles obtained in step (iii) to a predetermined peak particle size, the predetermined peak particle size being at or below 35 μm,
    or
    sieving the particles obtained in step (iii) to a predetermined peak particle size, the predetermined peak particle size being at or below 35 μm.

Fractionizing as performed in step (iv) should be interpreted in a broad sense as any method of fractionizing the MMC to a predetermined desired particle size distribution, typically and preferably characterized by a predetermined desired peak particle size. Fractionizing techniques include, but are not limited to, milling such as ball milling, pin-milling and jet-milling, or sieving such as vibrational sieving, or classification by weight. The fractionizing step may, if the MMC is loaded with other substance, for example a beneficial agent, alternatively be performed after the loading process.

According to one embodiment the method of the invention comprises loading the particulate MMC material with one or more agents.

The method comprises the steps of:
  a) dissolving an agent in a solvent;
  b) adding fractionized or non-fractionized MMC, to the agent solution of step (a); evaporating the solvent; and
  c) optionally drying the final product.
  d) fractionizing the loaded MMC to the desired particle size distribution, if not already fractionized prior to step b).

According to one embodiment of the invention the particulate MMC material is loaded with one or more active substances dissolved in an oily substance, wherein the increased ability to take up an oily substance is utilized as a way to load the particulate MMC material with the active substance. The method comprises adding, drop-wise, a beneficial agent (in the form of an oily substance or an agent dissolved in an oily substance), to the fractionized MMC during mixing, to obtain a 5-50 wt % (weight of beneficial agent per total weight of mixture of beneficial agent and MMC material) loading degree as desired by the application.

The particulate MMC material according to the invention has been tested according to a "Human repeated insult patch test" and can according to the result be considered as "Non Sensitizing", or "Hypoallergenic" or "Formulated to minimize the risks of allergy under normal way of use".

It is to be noted that elements of different embodiments described herein may freely be combined with each other unless such a combination is expressly stated as unsuitable, as will be readily understood by the person skilled in the art.

EXPERIMENTAL

Materials

Magnesium Oxide (LUVOMAG® M074, purchased from Lehmann & Voss & Co, Hamburg, Germany), methanol (<0.1% water, purchased from Stockmeier Chemie Dillenburg GmbH & Co. KG, Dillenburg, Germany) and carbon dioxide (3700150 carbon dioxide 2.5, purchased from Linde AG, Pullach, Germany) were used as purchased without further purification. Retinol (95%) and resveratrol (98%) were purchased from Chemtronica (Sollentuna, Sweden).

AIC Production

Magnesium oxide (MgO) and methanol was mixed under a pressure of 0.5-5 bar, at a temperature of 10-70° C. for 12-36 hours, providing a gel. The gel was then dried at a temperature of 50-105° C., providing particles. Finally, the particles were dried at a temperature up to 250° C.

Milling

Jet milling was performed in a fluidbed airjet mill, Netzsch Condux CGS 50 (Netzsch Lohnmahltechnik GmbH, Bobingen, Germany). Air was used as the carrier gas. Jet-mill set parameters typically used were: air nozzle 8 mm; air pressure 5.8 bar; air flow approximately 850 l/min; and sifter speed 2300 rpm. Material feed rates, depends on the other parameters as well as on the starting materials flowability and exact particle size distribution. Material feed rates exceeding 100 kg/h was reachable using as-synthesized material, with this equipment, in the manufacturing of the invented material. The skilled person understands that to achieve the desired particle sizes, or if one wants to use other equipment's or other setups, the parameters need to be fine-tuned accordingly, which is considered as normal engineering work Ball-milling was performed in a Retsch planetary ball mill PM400 (Retsch GmbH, Haan, Germany). Milling was performed under ambient conditions in a 125 ml milling jar, using 25 zirconia balls, 10 mm in diameter. Approximately 25 g of material was used for each milling setting. Ball milling was performed between 1 to 60 minutes using a speed of 200 rpm or between 2 to 10 minutes using a speed of 300 rpm.

Material Characterization

Pore size, pore volume and specific surface area (BET) were determined using nitrogen gas adsorption in a liquid nitrogen bath at 77 K. Measurements were made on a Gemini VII 2390 surface area and porosity analyzer (Micromeritics, Norcross, GA, USA), providing data to be used for determining pore size, pore volume and surface area of the particles, both without active substance (unloaded) and with active substance (loaded). Prior to analysis, samples were degassed for 12 hours at 105° C. under nitrogen gas flow in a FlowPrep060 Sample Degas System (Micromeritics, Norcross, GA, USA).

Pore size distributions were obtained using non-local density functional theory (NLDFT) applied to the adsorption branch of nitrogen sorption isotherms using a Carbon Pore Slit model ($\lambda=0.2$). The surface area was determined by using the well-recognized BET equation, and hence calculated from the nitrogen sorption isotherms (Brunauer et al, JACS, 60, 1938, 309-319).

Powder X-ray diffraction (XRD) patterns were obtained on a Bruker D8 Advance diffractometer (Bruker, AXS GmbH, Karlsruhe, Germany) with Ni-filtered Cu-K$\alpha$ radiation ($\lambda=1.54$ Å), generating XRD patterns through elastic X-ray scattering. Diffraction angles of 5-80 deg (2θ) were analyzed in steps of 0.02 deg with 0.2 s per step while rotating the sample. Prior to the analysis samples were ground with ethanol, dispersed onto zero-background silicon sample holders and placed under a lamp to evaporate the ethanol.

A Scanning Electron Microscope (SEM)—Zeiss Merlin instrument was utilized for the high resolution images of dry powders. This equipment is a High resolution FEG SEM for surface imaging. The SEM-images were obtained using the InLens detector at 2 kV acceleration voltage and a probe current of 80 pA. A small amount of powder was applied onto Al stubs with carbon tape by using a spatula. To decrease charging effect, a thin Cu-foil was applied at the edge of each Al-stub. Excess powder was blown off using air. A Polaron SC7640 sputter was used to coat the sample with gold. A coating sequence lasting for 40 s under 20 mA was used.

The particle size distributions were measured using laser diffraction with the Mastersizer 3000 (Malvern Panalytical, Ltd, Malvern, Great Britain), using a dry method with an Aero S accessory. The light scattering data, converted to particle size distribution were analyzed using Mie-scattering model, using the non-spherical particle type and $MgCO_3$ as material (i.e. $MgCO_3$ settings for the refractive index (1.717) and adsorption index (0.01)). Prior to adding the sample to the instrument, the sample container was mixed well in order to ensure good sampling. A few grams of powder was used for each measurement, the measurement time was set to 10-30 seconds. The lower obstruction limit was set to 0.5% and the upper limit to 5%, the air pressure was set to 1.5 barg. During the measurement the feed rate was constantly adjusted so that the obstruction was kept between 0.5 and 5%. All measurements were averaged and run at least five times.

Mattifying Effect Measurement

Mattifying effect on human skin was determined using a Skin-Glossymeter (GL 200 W, Courage+Khazaka Electronics GmbH, Koln, Germany). In the Skin-Glossymeter, parallel white light is emitted from the light emitting diode at a 600 angle to the skin surface and the reflected light is measured along with the diffuse scattering in separate channels. The values assessed in these channels were used to calculate a Gloss value which was converted into a Gloss value with diffuse scattering correction (Gloss DSC) to eliminate differences in skin color, texture and brightness. The Mattifying effect was calculated as $$\text{Mattifying effect } (\%) = \frac{\text{Gloss } DSC_{Reference} - \text{Gloss } DSC_{Material}}{\text{Gloss } DSC_{Reference}} \cdot 100,$$

where Gloss $DSC_{Reference}$ is the gloss DSC value measured on untreated skin and Gloss $DSC_{Material}$ is the gloss DSC value measured on an area on the skin where the material (powder) in interest had been applied.

The materials that were evaluated in the test were particulate MMC according to the invention, having a peak particle size of 7.2 μm, mesoporous silica (Making Cosmetics, Redmond, WA, USA), mica (Sericite GMS-4C; Kobo Products Inc, South Plainfield, NJ, USA), talc (VWR Chemicals, Radnor, PA, USA) and corn starch (Making Cosmetics, Redmond, WA, USA).

Oil Uptake Test

Oil uptake and oily substance uptake were measured by adding approximately 1 g of powder to a plastic weighing ship and then gradually adding olive oil by means of a pipette to the powder. The oil was thoroughly incorporated into the powder with a spatula. Addition of oil was continued until the paste was still hard with a matte finish. At this point the oil was added drop by drop to the powder and the paste was triturated with the spatula. Addition of oil was stopped when a firm, smooth and glossy paste was obtained. The mass of added oil when the paste still appeared non-glossy was noted. The oil uptake and oily substance uptake correspond to the mass of added oil to the mass of the powder (g/g). The oil uptake method has been derived from the standard test method for oil absorption of pigments by spatula rub-out (ASTM D281-95), a commonly used method in the industry. In the used oil uptake method, olive oil was used instead of linseed/flaxseed oil which is used in ASTM D281-95. Olive oil contains to large amounts fatty acids oleic and linoleic acid and therefore is by constitution very similar to linseed/flaxseed oil (main component linoleic acid). It has been verified in oil uptake tests using linseed oil (advocated by the standard) and olive oil that similar results are obtained.

Oil and Water Selectivity

Particulate MMC material with a peak particle size of 6 µm was portioned into aluminum weighing dishes, approximately 1 g in each dish, and dried at a temperature of 105° C. overnight. The mass of each sample was noted immediately after removal from the oven.

To determine the moisture uptake in samples containing different amounts of oil, an amount of between 0.1 and 0.5 g oil, in this case olive oil, per g particulate MMC was added to the dishes with the dried powder. The powder and oil mixtures were stirred with a spatula until homogeneous pastes were achieved. The samples were placed in a climate chamber, 20° C. and 76% relative humidity, for 24 hours to perform a moisture uptake test. A reference sample without oil addition was also placed in the climate chamber. The mass of each sample was noted after removal from the climate chamber. The moisture uptake corresponds to the ratio of the mass of absorbed water to the mass of the dry powder and is given in %.

To determine the oil uptake in samples containing different amounts of water, an amount of between 5 and 23 wt % of deionized water was added to the dishes with the dried powder. The powder and water were stirred with a spatula until homogenous. An oil uptake test, as described above, was performed. The oil uptake corresponds to the ratio of the mass of added oil to the mass of the dry powder and is given in g/g.

Loading by Solvent Evaporation

Trans-resveratrol and trans-retinol were loaded into particulate MMC material with a peak particle size of 6 µm to a loading degree of 30 wt % by solvent evaporation. Briefly, the agents were dissolved in ethanol followed by the addition of MMC. The solution was purged with nitrogen gas in a brown round bottom flask to protect the agent from oxygen and light. The solvent was evaporated in a rotary evaporator (Büchi Rotavapor R-200, Flawil, Switzerland) under reduced pressure (200 mbar) at 60° C. for 2-3 hours. The obtained product was further dried on a heating plate at 70° C. while flushing with nitrogen gas to protect the ingredients from oxygen. To analyze if the agents have entered the pores of the particulate MMC material, nitrogen gas adsorption (Gemini VII, Micrometrics, Georgia, USA). X-ray diffraction (XRD; D8 Advance, Bruker, Karlsruhe, Germany) analysis was performed, as described above, to show that the loaded MMC material was amorphous.

Results

Particle Size Distribution of MMC

Particulate MMC was synthesized as described above. MMC with different particle size distributions were prepared by milling the as-synthesized materials as described above. The particle size distribution was measured by laser diffraction as described above. The settings of the milling methods result in materials with different peak particle size, as well as distribution of particle sizes. FIG. 1a-b are graphs illustrating the particle size distribution for these two variants of MMC wherein (a) exhibit a peak particle size of 8 µm and a $D_{10}$-value of 1 µm, a $D_{50}$-value of 6 µm, a $D_{90}$-value of 14 µm and a $D_{98}$-value of 19 µm, and (b) a peak particle size of 98 µm and a $D_{10}$-value of 6 µm, a $D_{50}$-value of 44 µm, a $D_{90}$-value of 147 µm and a $D_{98}$-value of 209 µm.

Uptake of Oil, Oily Substance and Sebum as Well as Loading Capacity of MMC

Particulate MMC material samples with varying particle size were prepared to investigate the uptake of oil, oily substance and sebum as well as the loading capacity of the material. Details of preparation and measurements are given above. The results are presented in Table 1-2 and in FIGS. 2-4.

TABLE 1

Oil uptake for samples with different pore volume. Values given as mean and (s.d).

| Sample | Method | Peak particle size [µm] | D10 [µm] | D50 [µm] | D90 [µm] | D98 [µm] | Oil uptake [g/g] | Pore volume [cm³/g] | BET [m²/g] |
| --- | --- | --- | --- | --- | --- | --- | --- | --- | --- |
| 1 | Spray drying | 6.7 | 1.8 | 6.3 | 15.5 | 23.5 | 0.28 (0.01) | 0* | 1 |
| 2 | Ball-milling (dry) | 6.7 | 1.0 | 6.7 | 33.9 | 113.0 | 0.73 (0.03) | 0.23 | 133 |
| 3 | Jet-milling | 6.3 | 1.2 | 4.8 | 10.7 | 14.5 | 1.14 (N/A) | 0.46 | 245 |
| 4 | Ball-milling (wet) | 6.7 | 1.1 | 5.2 | 15.9 | 26.0 | 1.10 (0.01) | 0.47 | 434 |
| 5 | Jet-milling | 5.9 | 1.1 | 4.7 | 10.6 | 14.6 | 1.15 (N/A) | 0.47 | 285 |
| 6 | Jet-milling | 6.3 | 1.1 | 4.7 | 10.6 | 14.6 | 1.15 (N/A) | 0.47 | 285 |
| 7 | Jet-milling | 6.7 | 1.2 | 4.9 | 10.9 | 15.1 | 1.22 (N/A) | 0.47 | 312 |

TABLE 1-continued

Oil uptake for samples with different pore volume. Values given as mean and (s.d).

| Sample | Method | Peak particle size [μm] | D10 [μm] | D50 [μm] | D90 [μm] | D98 [μm] | Oil uptake [g/g] | Pore volume [cm³/g] | BET [m²/g] |
|---|---|---|---|---|---|---|---|---|---|
| 8 | Jet-milling | 8.1 | 1.3 | 6.0 | 13.9 | 19.2 | 1.06 (0.01) | 0.48 | 291 |
| 9 | Jet-milling | 6.3 | 1.2 | 4.9 | 10.8 | 14.9 | 1.17 (N/A) | 0.48 | 138 |
| 10 | Jet-milling | 6.3 | 1.1 | 4.7 | 10.1 | 13.7 | 1.15 (N/A) | 0.52 | 239 |
| 11 | Jet-milling | 7.2 | 1.2 | 5.0 | 10.7 | 14.3 | 1.06 (N/A) | 0.53 | 234 |
| 12 | Jet milling | 6.3 | 1.1 | 4.5 | 9.9 | 13.3 | 1.15 (0.002) | 0.53 | 367 |
| 13 | Jet-milling | 6.7 | 1.1 | 4.6 | 10.2 | 13.7 | 1.17 (N/A) | 0.53 | 241 |
| 14 | Jet-milling | 6.3 | 1.1 | 4.6 | 10.0 | 13.6 | 1.18 (0.02) | 0.53 | 361 |
| 15 | Jet-milling | 5.9 | 0.8 | 3.1 | 10.0 | 14.0 | 1.21 (0.01) | 0.54 | 494 |
| 16 | Jet-milling | 6.7 | 1.1 | 4.8 | 10.4 | 14.1 | 1.21 (N/A) | 0.55 | 169 |
| 17 | Jet milling | 6.3 | 1.1 | 4.7 | 10.4 | 14.2 | 1.22 (N/A) | 0.55 | 541 |
| 18 | Jet milling | 6.3 | 1.1 | 4.7 | 10.1 | 13.7 | 1.23 (N/A) | 0.55 | 542 |
| 19 | Jet milling | 6.3 | 1.2 | 4.8 | 10.2 | 13.7 | 1.24 (N/A) | 0.55 | 543 |
| 20 | Jet milling | 6.3 | 1.1 | 4.7 | 10.0 | 13.4 | 1.24 (N/A) | 0.55 | 539 |
| 21 | Jet milling | 6.3 | 1.1 | 4.7 | 10.1 | 13.6 | 1.21 (N/A) | 0.56 | 542 |
| 22 | Jet milling | 6.7 | 1.2 | 4.9 | 10.3 | 13.8 | 1.22 (N/A) | 0.56 | 547 |
| 23 | Jet milling | 6.3 | 1.1 | 4.8 | 10.2 | 13.7 | 1.22 (N/A) | 0.56 | 544 |
| 24 | Jet milling | 6.3 | 1.1 | 4.7 | 9.9 | 13.2 | 1.23 (N/A) | 0.56 | 534 |
| 25 | Jet milling | 6.3 | 1.1 | 4.6 | 10.0 | 13.5 | 1.25 (N/A) | 0.56 | 545 |
| 26 | Jet milling | 7.2 | 1.2 | 5.0 | 10.8 | 14.5 | 1.28 (N/A) | 0.57 | 477 |
| 27 | Jet milling | 6.7 | 1.2 | 4.9 | 10.3 | 13.7 | 1.29 (N/A) | 0.57 | 487 |
| 28 | Jet milling | 7.2 | 1.2 | 4.9 | 10.6 | 14.2 | 1.30 (N/A) | 0.58 | 494 |
| 29 | Jet-milling | 9.9 | 0.9 | 5.3 | 17.8 | 26.0 | 1.18 (0.01) | 0.60 | 535 |
| 30 | Vibrational sieving | 7.6 | 1.4 | 6.2 | 19.4 | 30.7 | 1.45 (0.03) | 0.90 | 385 |

*Non-porous material.

TABLE 2

Oil uptake for samples with different particle size. Values given as mean and (s.d).

| Sample | Method | Peak particle size [μm] | D10 [μm] | D50 [μm] | D90 [μm] | D98 [μm] | Oil uptake [g/g] | Pore volume [cm³/g] | BET [m²/g] |
|---|---|---|---|---|---|---|---|---|---|
| 1 | Jet-milling | 5.9 | 0.8 | 3.1 | 10.0 | 14.0 | 1.21 (0.01) | 0.54 | 494 |
| 2 | Jet-milling | 6.3 | 1.2 | 4.9 | 10.8 | 14.9 | 1.17 (N/A) | 0.48 | 138 |
| 3 | Jet-milling | 6.3 | 1.2 | 4.8 | 10.7 | 14.5 | 1.14 (N/A) | 0.46 | 245 |
| 4 | Jet-milling | 6.3 | 1.1 | 4.7 | 10.6 | 14.6 | 1.15 (N/A) | 0.47 | 285 |
| 5 | Jet milling | 6.3 | 1.1 | 4.7 | 10.1 | 13.7 | 1.15 (N/A) | 0.52 | 239 |
| 6 | Jet milling | 6.3 | 1.1 | 4.5 | 9.9 | 13.3 | 1.15 (0.002) | 0.53 | 367 |

TABLE 2-continued

Oil uptake for samples with different particle size. Values given as mean and (s.d).

| Sample | Method | Peak particle size [μm] | D10 [μm] | D50 [μm] | D90 [μm] | D98 [μm] | Oil uptake [g/g] | Pore volume [cm³/g] | BET [m²/g] |
|---|---|---|---|---|---|---|---|---|---|
| 7 | Jet milling | 6.3 | 1.1 | 4.6 | 10.0 | 13.6 | 1.18 (0.02) | 0.53 | 361 |
| 8 | Jet milling | 6.3 | 1.1 | 4.7 | 10.4 | 14.2 | 1.22 (N/A) | 0.55 | 541 |
| 9 | Jet milling | 6.3 | 1.1 | 4.7 | 10.1 | 13.7 | 1.23 (N/A) | 0.55 | 542 |
| 10 | Jet milling | 6.3 | 1.2 | 4.8 | 10.2 | 13.7 | 1.24 (N/A) | 0.55 | 543 |
| 11 | Jet milling | 6.3 | 1.1 | 4.7 | 10.0 | 13.4 | 1.24 (N/A) | 0.55 | 539 |
| 12 | Jet milling | 6.3 | 1.1 | 4.7 | 10.1 | 13.6 | 1.21 (N/A) | 0.56 | 542 |
| 13 | Jet milling | 6.3 | 1.1 | 4.8 | 10.2 | 13.7 | 1.22 (N/A) | 0.56 | 544 |
| 14 | Jet milling | 6.3 | 1.1 | 4.7 | 9.9 | 13.2 | 1.23 (N/A) | 0.56 | 534 |
| 15 | Jet milling | 6.3 | 1.1 | 4.6 | 10.0 | 13.5 | 1.25 (N/A) | 0.56 | 545 |
| 16 | Jet-milling | 6.7 | 1.2 | 4.9 | 10.9 | 15.1 | 1.22 (N/A) | 0.47 | 312 |
| 17 | Jet milling | 6.7 | 1.1 | 4.6 | 10.2 | 13.7 | 1.17 (N/A) | 0.53 | 241 |
| 18 | Jet milling | 6.7 | 1.1 | 4.8 | 10.4 | 14.1 | 1.21 (N/A) | 0.55 | 169 |
| 19 | Jet milling | 6.7 | 1.2 | 4.9 | 10.3 | 13.8 | 1.22 (N/A) | 0.56 | 547 |
| 20 | Jet milling | 6.7 | 1.2 | 4.9 | 10.3 | 13.7 | 1.29 (N/A) | 0.57 | 487 |
| 21 | Jet milling | 7.2 | 1.2 | 5.0 | 10.7 | 14.3 | 1.06 (N/A) | 0.53 | 234 |
| 22 | Jet milling | 7.2 | 1.2 | 5.0 | 10.8 | 14.5 | 1.28 (N/A) | 0.57 | 477 |
| 23 | Jet milling | 7.2 | 1.2 | 4.9 | 10.6 | 14.2 | 1.30 (N/A) | 0.58 | 494 |
| 24 | Jet-milling | 8.1 | 1.3 | 6.0 | 13.9 | 19.0 | 1.06 (0.01) | 0.48 | 291 |
| 25 | Jet-milling | 9.9 | 0.9 | 5.3 | 17.8 | 26.0 | 1.18 (0.01) | 0.60 | 535 |
| 26 | Ball-milling | 31.1 | 1.9 | 17.5 | 70.6 | 191 | 0.91 (N/A) | 0.46 | 499 |
| 27 | Ball-milling | 35.3 | 2.3 | 19.6 | 95.6 | 234 | 0.96 (N/A) | 0.47 | 417 |
| 28 | Ball-milling | 40.1 | 2.0 | 19.6 | 79.3 | 171 | 0.96 (N/A) | 0.73 | 552 |
| 29 | Ball-milling | 45.6 | 2.6 | 23.4 | 86.6 | 162 | 0.98 (N/A) | 0.55 | 588 |
| 30 | Ball-milling | 45.6 | 2.5 | 22.2 | 84.6 | 182 | 0.98 (N/A) | 0.35 | 328 |
| 31 | Ball-milling | 51.8 | 2.8 | 24.3 | 98.6 | 166 | 0.94 (0.01) | 0.48 | 258 |
| 32 | Ball-milling | 55.4 | 3.6 | 28.5 | 97.5 | 146 | 0.96 N/A) | 0.60 | 305 |
| 33 | Ball-milling | 58.9 | 4.5 | 32.7 | 109 | 176 | 1.00 N/A) | 0.58 | 621 |
| 34 | Ball-milling | 66.9 | 3.9 | 30.6 | 114 | 177 | 0.99 N/A) | 0.66 | 571 |
| 35 | Ball-milling | 76.0 | 5.5 | 39.9 | 135 | 200 | 0.97 N/A) | 0.57 | 581 |
| 36 | Ball-milling | 98.1 | 6.0 | 43.5 | 147 | 209 | 0.92 (0.01) | 0.54 | 590 |

FIGS. 2 *a* and *b* are graphs illustrating the oil uptake as a function of total pore volume a) and BET surface area b) for particulate MMC according to the invention having particles with a peak particle size between 6 and 10 μm. The oil uptake appears to increase with the total pore volume but is clearly less dependent on surface area. When particulate MMC according to the invention has obtained some appreciable surface area (>140 m²/g), the oil uptake appears to be close to constant.

FIG. 3 is a graph illustrating the oil uptake as a function of peak particle size for milled materials (ball-milling and jet-milling) for particulate MMC according to the invention. Dotted line used as a guide for the eye. As seen in the graph the oil uptake appears not to be affected by increasing peak particle size for sizes larger than 35 μm. However, for small particle sizes, with an onset around 35 μm, a significant increase in oil uptake is demonstrated. The increase in oil uptake is evident also from examining the $D_{10}$, $D_{50}$ and $D_{90}$-values as illustrated in the graphs of FIGS. 4 *a-c*. The onset corresponds to a $D_{10}$-value of 3 μm, a $D_{50}$-value of 20 μm and a $D_{90}$-value of 96 μm.

Characterization of Different Materials after Oil Uptake

The oil uptake of five different materials was investigated: mesoporous silica, starch, talc, kaolin and particulate MMC according to the invention. The same amounts of oil, in this case olive oil, was added to the materials and the oil was homogenously blended into the materials with a spatula. The amounts were 0, 0.25, 0.50, 0.75, 1.0 and 1.25 g oil/g material, or until the material became a paste. Photographs and SEM images were used to classify the materials according to visual and sensory characteristics, which may also indicate what product type, considering the powder characteristics, the composition may be used for. A loose powder or powder spray product require a dry powder, a pressed powder product may contain an oily powder, a semi-solid or a liquid product may contain a wet paste. The data is presented in Table 3 and in FIG. 5 *a-o*.

TABLE 3

Visual and sensory assessment of materials with different oil additions.

| Sample | Material | Amount oil [g oil/g material] | Visual and sensory characteristics |
|---|---|---|---|
| 1 | Mesoporous Silica | 0 | Dry powder |
| 2 | Mesoporous Silica | 0.25 | Dry powder |
| 3 | Mesoporous Silica | 0.50 | Non-oily, partly agglomerated powder |
| 4 | Mesoporous Silica | 0.75 | Oily powder |
| 5 | Mesoporous Silica | 1.00 | Wet paste |
| 6 | Starch | 0 | Dry powder |
| 7 | Starch | 0.25 | Oily powder |
| 8 | Starch | 0.50 | Wet paste |
| 9 | Talc | 0 | Dry powder |
| 10 | Talc | 0.25 | Oily powder |
| 11 | Talc | 0.50 | Wet paste |
| 12 | Kaolin | 0 | Dry powder |
| 13 | Kaolin | 0.25 | Oily powder |
| 14 | Kaolin | 0.50 | Wet paste |
| 15 | Particulate MMC | 0 | Dry powder |
| 16 | Particulate MMC | 0.25 | Dry powder |
| 17 | Particulate MMC | 0.50 | Dry powder |
| 18 | Particulate MMC | 0.75 | Non-oily, partly agglomerated powder |
| 19 | Particulate MMC | 1.00 | Oily powder |
| 20 | Particulate MMC | 1.25 | Wet paste |

Figure 5A:
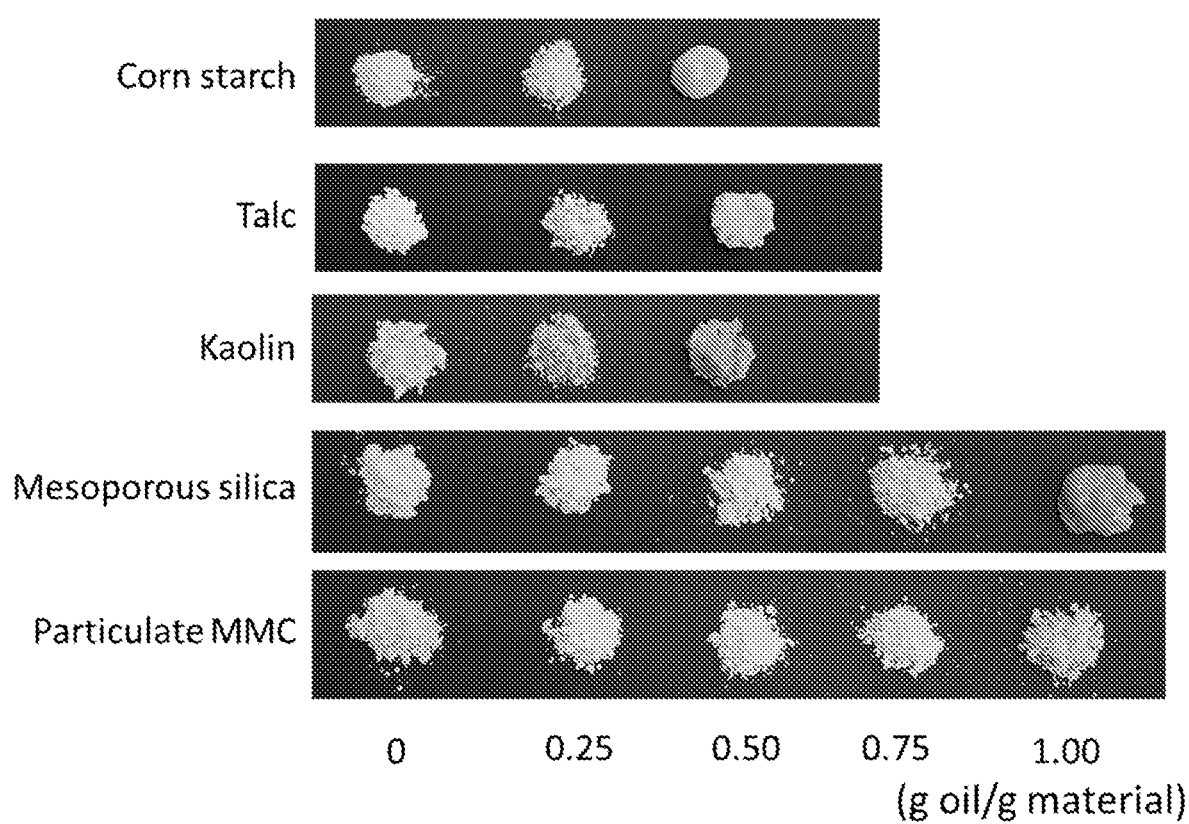

FIG. 5*a* shows photographs of different materials (corn starch, talc, kaolin, mesoporous silica, and particulate MMC according to the invention), both pure (non-mixed) and mixed with increasing amounts of olive oil. In FIG. 5 *b-o* SEM images of un-mixed materials and oil-mixed materials are displayed. In FIG. 5 *b-f* SEM images of pure materials are shown; particulate MMC according to the invention (b), pure mesoporous silica (c), pure kaolin (d), pure talc (e), and pure corn starch (f). Figure g-k display SEM images of the materials mixed with 0.25 g oil/g material; MMC according to the invention (g), mesoporous silica (h), kaolin (i), talc (j) and corn starch (k). FIG. 5 *l-m*) display SEM images of particulate MN/C according to the invention (l) and mesoporous silica (in) mixed with 0.50 g oil/g material. FIG. 5 *n-o*) display SEM images of particulate MN/C according to the invention (n) and mesoporous silica (o) mixed with 0.75 g oil/g material. The white or shiny parts in the images stem from charge buildup due to the low conductivity of the oil and is therefore significant of an oily paste formed by the powder particles and oil, well visible at the magnification used to obtain the SEM-images.

The SEM images confirm the visual and sensory assessment of the pure and oil mixed powders. Particulate MMC according to the invention, remains a completely dry powder consisting of free powder particles up to a load of 0.5 g oil/g MMC powder (FIG. 5 *b, g, l*). At 0.75 g oil/g MMC powder, partial agglomeration occurs (FIG. 5 *n* shows a non-agglomerated region) but the powder remains non-oily with no observed shine/white patches due to oil film/oil paste formation.

This is in large contrast to the nonporous materials kaolinite, talc and corn starch which form a paste of oil and powder particles already at 0.25 g oil/g material (FIG. 5 *d, e, f*). Furthermore, the particles are at 0.25 g oil/g material no longer well-defined separate particles as is the case for the pure materials (FIG. 5 *h, i, j*). Mesoporous silica is capable of higher absorption of oil than the nonporous materials, remaining a dry powder up to 0.5 g oil/g silica (FIG. 5 *c, h, m*) but the formation of an oily powder at 0.75 g oil/g silica is well visible by a shiny appearance and agglomerated silica particles as exemplified in FIG. 5 *n*. MMC and mesoporous silica mixed to 1 g/g material were not analyzed in SEM due to the risk of filament contamination.

The ability of the particulate MMC according to the invention to take up and hold oily substances up to significantly higher concentrations with the powder characteristics preserved compared to common prior art materials used as cosmetic ingredients may be advantageously utilized to provide new topological and cosmetic powder formulation products. With particulate MMC, a loose powder product can be provided wherein the particulate MMC has taken up an oily substance up to a concentration of 0.75 g oil/g MMC powder. Similarly, a powder spray product may be provided comprising particulate MMC that has taken up an oily substance at a concentration up to 0.75 g oil/g MMC powder, or at least up to 0.5 g oil/g MMC powder. A pressed powder product, wherein the particulate MMC has taken up an oily substance up to 0.75 g oil/g MMC powder, and for some applications up to 1.0 g oil/g MMC powder, can be provided. Also in products which are not in powder form the ability of particulate MMC to receive and hold oily substances to very high concentrations may be utilized to provide formulations previously difficult or impossible to realize. Such products include, but is not limited to a semi-solid product comprising particulate MMC that has taken up an oily substance up to 1.25 g oil/g MMC powder, or at least up to 1.0 g oil/g MMC powder, and a liquid product comprising particulate MMC that has taken up an oily substance up to 1.25 g oil/g MMC powder, or at least up to 1.0 g oil/g MMC powder.

Oil and Water Selectivity of MMC

Particulate MMC was synthesized as described above. Samples with different amounts of oil were prepared to study the moisture uptake of the particulate MMC material when the material had been mixed with oil. Vice versa, samples containing different amounts of water were prepared to study the oil uptake of the particulate MMC material when the material had already absorbed water. FIG. 6*a-b* show the oil uptake after addition of water to the particulate MMC (a) and the moisture uptake after the particulate MMC had already been mixed with oil (b). The particulate MMC has still the capacity to absorb moisture when it is mixed with oil as well as a capacity to take up oil when it contains water.

Particulate MMC Loaded with Active Substance

Particulate MMC was synthesized as described above. Trans-resveratrol and trans-retinol, being examples of active substances, were loaded into the particulate MMC by solvent evaporation. FIG. 7a shows XRD patterns of the particulate MMC according to the invention (top), the particulate MMC loaded with trans-resveratrol (middle) and pure crystalline trans-resveratrol (bottom). FIG. 7b is a graph of the pore volume as a function of pore size; for the particulate MMC (solid line) and the particulate MMC loaded with trans-resveratrol (dashed line). FIG. 8a shows XRD patterns of the particulate MMC according to the invention (top), the particulate MMC loaded with trans-retinol (middle) and pure trans-retinol (bottom). FIG. 8b is a graph of the pore volume as a function of pore size; for the particulate MMC (solid line) and the particulate MMC loaded with trans-retinol (dashed line). The data for pure crystalline trans-retinol was obtained from Kim, D.-G., et al., *Retinol-encapsulated low molecular water-soluble chitosan nanoparticles*. International Journal of Pharmaceutics, 2006. 319(1): p. 130-138.

FIGS. 7 a and 8 a show that the free active ingredients exhibit crystalline peaks in the X-ray diffractograms, whereas when loaded into the particulate MMC material the loaded material has an amorphous nature (the crystalline peaks correspond to crystalline MgO). Trans-resveratrol and trans-retinol were successfully loaded into the particulate MMC, as can be seen by a reduction in pore volume, as seen in FIGS. 7 b and 8 b, respectively.

Mattifying Effect of Particulate MMC and Four Reference Materials

A screening test was first performed to select a test group consisting of test subjects having normal to oily forehead skin. From the screening test the subjects with the most oily skin were chosen as the final test group to evaluate the mattifying effect of different absorbing powder materials: particulate MMC according to the invention according to the invention, mesoporous silica, mica, talc and corn starch. A minimum of 9 test subjects and a maximum of 13 test subjects tested each material. All test subjects applied a normal usage dose of powder on the right side of the forehead using a clean brush applicator. The left side of the forehead was left untreated and used as reference skin. The two sides were separated by a piece of surgical tape during application of the powders. The gloss value was measured at 9 different points in the center of each side of the forehead approximately 15-25 min after application of the powder. The probe was wiped off with a tissue paper in between measuring the reference and material sides to avoid contamination. Average Gloss DSC values were calculated from the 9 measurements from each side of the forehead and the Mattifying effect for each test subject was then calculated as described above. An average Mattifying effect for each material was calculated from all test subjects. The peak particle size of all materials was measured as described above.

Figure 9:
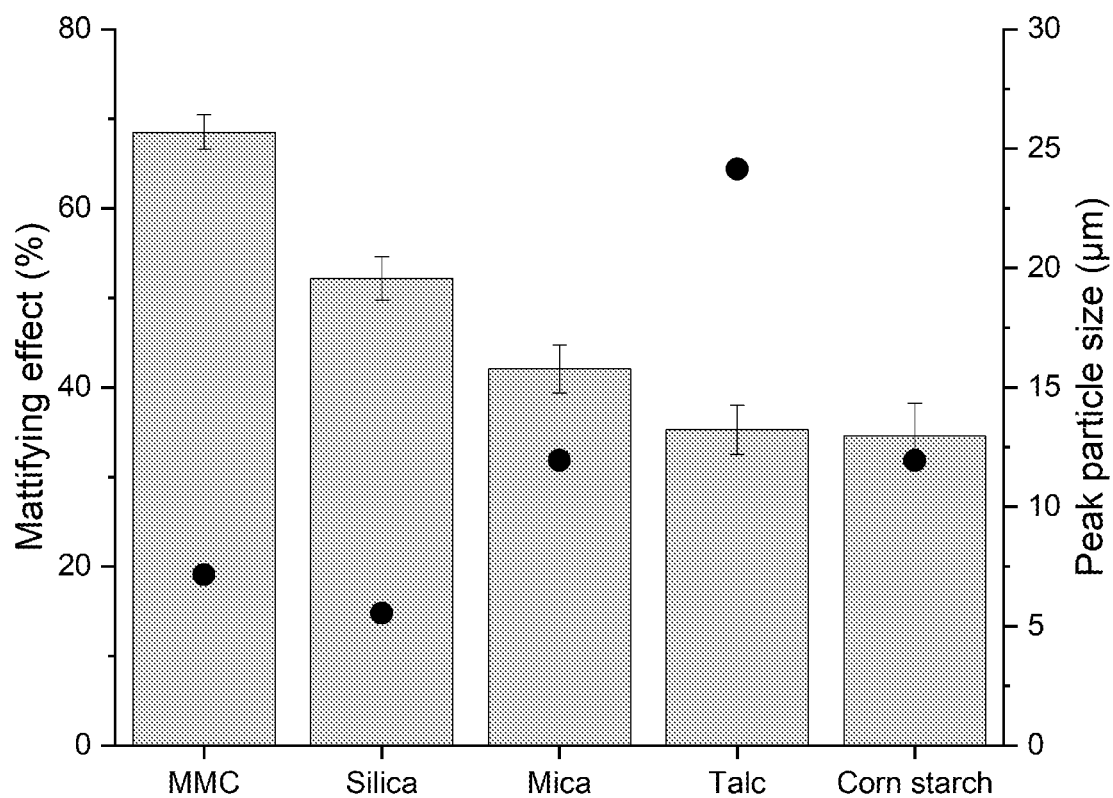
FIG. 9: Mattifying effect (shown as grey bars) and peak particle size (shown as black circles) of particulate MMC according to the invention, mesoporous silica, mica, talc and corn starch.

The mattifying effect of the different materials as well as the peak particle size is presented in FIG. 9 and in table 4. The particulate MMC, according to the invention, exhibit a mattifying effect of approximately 68% (decrease in gloss value), which represents a noticeable increase compared to the today commonly used mattifying materials.

TABLE 4

Mattifying effect for materials with different particle size.
Values given as mean and (s.d).

| Sample | Material | Mattifying effect [%] | Peak particle size [μm] | $D_{10}$ [μm] | $D_{50}$ [μm] | $D_{90}$ [μm] | $D_{98}$ [μm] |
|---|---|---|---|---|---|---|---|
| 1 | Particulate MMC | 68.5 (1.9) | 7.2 | 1.2 | 5.1 | 12.6 | 17.6 |
| 2 | Mesoporous silica | 52.2 (2.4) | 5.6 | 2.2 | 5.2 | 9.1 | 11.2 |
| 3 | Mica | 42.1 (2.7) | 11.9 | 3.5 | 10.8 | 28.4 | 47.6 |
| 4 | Talc | 35.3 (2.7) | 24.1 | 4.3 | 18.6 | 56.8 | 85.0 |
| 5 | Corn starch | 34.6 (3.7) | 11.9 | 7.8 | 12.1 | 18.3 | 22.1 |

The invention claimed is:

1. A particulate amorphous mesoporous magnesium carbonate material suitable for taking up oily substances, wherein the particulate amorphous mesoporous magnesium carbonate material has a total pore volume larger than 0.1 $cm^3/g$, a specific surface area larger than 100 $m^2/g$ and is constituted of particles having a peak particle size between 1 and 20 μm.

2. The particulate amorphous mesoporous magnesium carbonate material according to claim 1, wherein the total pore volume of the particulate amorphous mesoporous magnesium carbonate material is larger than 0.2 $cm^3/g$.

3. The particulate amorphous mesoporous magnesium carbonate material according to claim 1, wherein the D90 value is below 96 μm.

4. The particulate amorphous mesoporous magnesium carbonate material according to claim 1, wherein the particulate amorphous mesoporous magnesium carbonate material is capable of an uptake of an oily substance above 0.5 g oil/g particulate amorphous mesoporous magnesium carbonate material, when the particulate amorphous mesoporous magnesium material contains at least 5 wt % moisture.

5. The particulate amorphous mesoporous magnesium carbonate material according to claim 1, wherein the particulate amorphous mesoporous magnesium carbonate material is loaded with an agent.

6. The particulate amorphous mesoporous magnesium carbonate material according to claim 5, wherein the agent is an oily substance.

7. The particulate amorphous mesoporous magnesium carbonate material according to claim 5, wherein the agent is a beneficial agent.

8. The particulate amorphous mesoporous magnesium carbonate material according to claim 5, wherein the agent is an active substance.

9. The particulate amorphous mesoporous magnesium carbonate material according to claim 8, wherein the active substance is an active pharmaceutical agent.

10. A topical composition comprising the particulate amorphous mesoporous magnesium carbonate material according to claim 1.

11. A cosmetic composition comprising the particulate amorphous mesoporous magnesium carbonate material according to claim 1.

12. A loose powder product comprising the particulate amorphous mesoporous magnesium carbonate material according to claim 1 mixed with an oily substance at a concentration up to 0.75 g oil/g particulate amorphous mesoporous magnesium carbonate material.

13. A powder spray product comprising the particulate amorphous mesoporous magnesium carbonate material according to claim 1 mixed with an oily substance at a concentration up to 0.75 g oil/g particulate amorphous mesoporous magnesium carbonate material.

14. A pressed powder product comprising the particulate amorphous mesoporous magnesium carbonate material according to claim 1 mixed with an oily substance at a concentration up to 1.0 g oil/g particulate amorphous mesoporous magnesium carbonate material.

15. A semi-solid product comprising the particulate amorphous mesoporous magnesium carbonate material according to claim 1 mixed with an oily substance at a concentration up to 1.25 g oil/g particulate amorphous mesoporous magnesium carbonate material.

16. A liquid product comprising the particulate amorphous mesoporous magnesium carbonate material according to claim 1 mixed with an oily substance at a concentration up to 1.25 g oil/g particulate amorphous mesoporous magnesium carbonate material.

17. A mattifying agent in an oily composition comprising the particulate amorphous mesoporous magnesium carbonate material according to claim 1.

18. A method of producing a particulate amorphous mesoporous magnesium carbonate material according to claim 1 comprising the steps of:
   providing an amorphous mesoporous magnesium carbonate material with a total pore volume larger than 0.1 $cm^3/g$, a specific surface area between 100 and 800 $m^2/g$; and
   fractionizing the amorphous mesoporous magnesium carbonate material to form a particulate amorphous mesoporous magnesium carbonate material wherein the particle distribution has a peak particle size between 1 and 20 μm.

19. The method of producing a particulate amorphous mesoporous magnesium carbonate material according to claim 18, wherein the step of fractionizing comprises milling the amorphous mesoporous magnesium carbonate material.

20. The particulate amorphous mesoporous magnesium carbonate material according to claim 3, wherein the total pore volume of the particulate amorphous mesoporous magnesium carbonate material is larger than 0.3 $cm^3/g$.

21. A particulate amorphous mesoporous magnesium carbonate material suitable for taking up oily substances, wherein the particulate amorphous mesoporous magnesium carbonate material and is constituted of particles having a peak particle size between 1 and 20 μm,
   wherein the particulate amorphous mesoporous magnesium carbonate material has a total pore volume 0.46 to 0.60 $cm^3/g$ and a specific surface area larger than 258 to 621 $m^2/g$, and
   wherein the particulate amorphous mesoporous magnesium carbonate material has an uptake of an oily substance of 1.14 to 1.28 g oil/g particulate amorphous mesoporous magnesium carbonate material.

* * * * *